(12) United States Patent
Sakai et al.

(10) Patent No.: US 7,041,656 B2
(45) Date of Patent: May 9, 2006

(54) SULFATED FUCOGLUCURONOMANNAN

(75) Inventors: Takeshi Sakai, Aomori (JP); Hitomi Kimura, Aomori (JP); Katsushige Ikai, Shiga (JP); Ikunoshin Kato, Kyoto (JP)

(73) Assignee: Takara Bio Inc., Shiga (JP)

( * ) Notice: Subject to any disclaimer, the term of this patent is extended or adjusted under 35 U.S.C. 154(b) by 194 days.

(21) Appl. No.: 10/475,346

(22) PCT Filed: Apr. 18, 2002

(86) PCT No.: PCT/JP02/03853

§ 371 (c)(1),
(2), (4) Date: Oct. 20, 2003

(87) PCT Pub. No.: WO02/086116

PCT Pub. Date: Oct. 31, 2002

(65) Prior Publication Data

US 2005/0090456 A1 Apr. 28, 2005

(30) Foreign Application Priority Data

Apr. 18, 2001 (JP) ............................. 2001-119671
May 24, 2001 (JP) ............................. 2001-155849

(51) Int. Cl.
*A61K 31/715* (2006.01)
*A61K 31/70* (2006.01)
*C07H 3/06* (2006.01)

(52) U.S. Cl. ............................. 514/61; 514/23; 514/54; 536/123.1; 536/124

(58) Field of Classification Search .................. 514/61, 514/23, 54; 536/123.1, 124; 435/200
See application file for complete search history.

(56) References Cited

U.S. PATENT DOCUMENTS

| 4,975,533 | A | 12/1990 | Kondo et al. |
| 6,054,577 | A | 4/2000 | Sakai et al. |
| 6,207,652 | B1 | 3/2001 | Sakai et al. |
| 6,489,155 | B1 * | 12/2002 | Takayama et al. .......... 435/200 |

FOREIGN PATENT DOCUMENTS

JP 7-59563 3/1995

OTHER PUBLICATIONS

Hitomi Kimura et al, "Structures of Sulfated Fucoglucronomannan Oligosaccharides Derived from *Fucus vesiculosis* Generated Using Sulfated Fucoglucronomannan Lyase Produced by *Fucophilus fucoidanolyticus*", The 5th, Japanese Society for Marine Biotechnology Taikai (Marine Bio Shizuoka 2000), Abstracts, May 24, 2001, pp. 71.

Elizabeth Percival et al, "Structural Studies of the Water-Soluble Fucan from *Lessonia nigrescens*", Carbohydrate Research, 1984, vol. 125, pp. 283-329, Elsevier Science Publishers B.V., Amsterdam, printed in the Netherlands.

* cited by examiner

Primary Examiner—Samuel Barts
Assistant Examiner—Michael C. Henry
(74) Attorney, Agent, or Firm—Browdy and Neimark, PLLC

(57) ABSTRACT

An enzyme which decomposes a sulfated fucoglucuronomannan and is useful in the field of glycotechnology; a process for producing the enzyme; a fucoidan fraction reduced in the number of the kinds of molecules and useful as a reagent in glycotechnology; a sulfated fucoglucuronomannan oligosaccharide; and processes for producing the fraction and oligosaccharide.

1 Claim, 14 Drawing Sheets

```
                        SEQUENCE LISTING

<160> NUMBER OF SEQ ID NOS: 1

<210> SEQ ID NO 1
<211> LENGTH: 1535
<212> TYPE: DNA
<213> ORGANISM: Fucophilus fucoidanolyticus SI-1234

<400> SEQUENCE: 1
ggatccgata gagtttgatc ctggctcaga gtgaacgctg gcggcgtggt taagacatgc     60
aagtcgaacg agattctttg tattgaagcc tcggtggatt tataaagatg aaagtggcaa    120
acgggtgcgt aacacgtgag caatctgccc taaagatcgg aatagctcga ggaaactcga    180
attaatgccg gatgtgatac gccaactcat gttggtagta ttaaagcttg taatggcgct    240
ttaggaggag ctcgcggcct atcagcttgt tggtgaggta aaggctcacc aaggcaaaga    300
cgggtagctg gtctgagagg atgatcagcc acactggaac tgagacacgg tccagacacc    360
tacgggtggc agcagtttcg aatcattcac aatgggggca accctgatgg tgcaacgccg    420
cgtgagggat gaaggccttc gggtcgtaaa cctctgtcac cagggagcaa caagcaggtt    480
catagcctgc cctgagttaa cctggagagg aagcagtggc taactccgtg ccagcagccg    540
cggtaatacg gagactgcaa gcgttactcg gattcactgg gcgtaaaggg tgcgtaggcg    600
gatagatgtg tcaggtgtga aatctcgggg ctcaacctcg aaactgcgcc tgaaactgtc    660
tatctagagt attggagggg taagcggaat ttctggtgta gcggtgaaat gcgtagatat    720
cagaaggaac accaatggcg aaggcagctt actggacaaa tactgacgct gaggcacgaa    780
agcatgggta gcgaaaggga ttagataccc ctgtagtcca tgccgtaaac gttgcacact    840
aggtcttggg ggtttcgacc ctttcaggac cccagctaac gcgataagtg tgccgcctga    900
ggactacggc cgcaaggcta aaactcaaag gaattgacgg gggcccgcac aagcggtgga    960
gcatgtggtt taattcgatg caacgcgaag aaccttacct aggcttgaca tgtaatggac   1020
gattttcaga gatgaatttt tcccttcggg gctgttacac aggtgctgca tggccgtcgt   1080
cagctcgtgt cgtgagatgt ttggttaagt ccagcaacga gcgcaaccct cgtccttagt   1140
tgccagcacg taatggtggg gactctaagg agacaaactc tctttgagag tgggaaggtg   1200
gggatgacgt caggtcagta tggcccttac gcctagggct acacacgtgc tacaatgccc   1260
ggtacaatag gacgcaatac cgcgaggtgg agcaaatcct caaaaccggg cccagttcgg   1320
attggagtct gcaactcgac tccatgaagt cggaatcgct agtaatgacg tatcagctat   1380
gacgtcgtga atacgttccc gggccttgta cacaccgccc gtcacatcat gaaagccggt   1440
tttgcccgaa gtacgtgagc tatccctcgg gaggcagcgt cctaaggcag ggctggtgat   1500
tgggatgaag tcgtaacaag gtagccatcc atatg                              1535
```

SULFATED FUCOGLUCURONOMANNAN

TECHNICAL FIELD

The present invention relates to a sulfated fucoglucuronomannan-degrading enzyme which is useful in a field of glycotechnology and a method for producing the enzyme, as well as a fucoidan fraction containing less molecular species and a sulfated fucoglucuronomannan oligosaccharide which are useful as reagents for glycotechnology and methods for producing the same.

BACKGROUND ART

Brown algae contain a variety of sulfated polysaccharides. These sulfated polysaccharides are often generically called fucoidans or fucoidins. Their structures vary depending on the algae from which they derive. For example, sulfated polysaccharides extracted from algae of the order Fucales, *Kjellmaniella crassifolia* Miyabe, *Laminaria japonica* Areschoug, *Cladosiphon okamuranus* Tokida, *Nemacystus decipiens* (Suringar) Kuckuck and sporophyll of *Undaria pinnatifida* (Harvey) Suringar have structures different from each other. In general, a sulfated polysaccharide fraction prepared from one alga contains a mixture of several sulfated polysaccharide molecular species.

Sulfated polysaccharide molecular species of which the structures have been determined include sulfated fucans, sulfated fucoglucuronomannans, sulfated fucogalactans and sulfated glucuronofucans. Sulfated polysaccharides generally have some biological activities in many cases. For example, a sulfated fucan fraction has been reported to have a strong anticoagulant activity, and a sulfated fucoglucuronomannan fraction has been reported to have an apoptosis inducing activity against tumor cells. Therefore, attempts have been made in order to develop a pharmaceutical using a sulfated polysaccharide.

If one intends to develop a pharmaceutical using a sulfated polysaccharide, it is necessary to determine its structure. Use of an enzyme that degrades the sulfated polysaccharide is very advantageous for the determination of the structure. However, no enzyme that degrades a sulfated polysaccharide derived from a brown alga is commercially available. Furthermore, an enzyme that specifically degrades the sulfated polysaccharide is required in order to determine the structure of the sulfated polysaccharide. This is because sulfated polysaccharides derived from brown algae vary depending on the species of the algae.

A sulfated polysaccharide mixture derived from an alga of the order Fucales has been reported to have an anticoagulant activity, an activity of inhibiting colonization by a chlamydia onto uterine epidermal cells, an activity of suppressing an allergic reaction, an activity of suppressing grafted organ rejection and the like. Structures of fucoidans derived from algae of the order Fucales have been studied in order to elucidate the relationship between the activities and the structures. However, only average values for the structures have been proposed based on physicochemical analyses.

Several kinds of sulfated polysaccharide molecular species are present in a sulfated polysaccharide mixture fraction prepared from an alga of the order Fucales. Sulfated polysaccharides other than the molecular species that is responsible for the biological activity of interest are generally unnecessary. In some cases, such unnecessary molecular species may induce ill effects.

It would be very useful for elucidating the relationship between the biological activities and the structures if one could prepare oligosaccharides from a sulfated polysaccharide derived from an alga of the order Fucales with structural reproducibility. For example, an enzyme that degrades a sulfated fucoglucuronomannan contained in a sulfated polysaccharide mixture fraction derived from a brown alga to generate oligosaccharides is known (WO 96/34004). This enzyme acts well on a sulfated fucoglucuronomannan derived from a brown alga of the order Laminariales to generate sulfated fucoglucuronomannan oligosaccharides. However, it has almost no activity on a sulfated fucoglucuronomannan derived from a brown alga of the order Fucales.

For the reasons as described above, an enzyme that specifically degrades a molecular species contained in a sulfated polysaccharide mixture fraction derived from a brown alga of the order Fucales, a fucoidan fraction comprising more homogeneous molecular species, an oligosaccharide having an homogeneous structure produced by an enzymatic means, and methods for producing the same have been desired.

OBJECTS OF INVENTION

The main object of the present invention is to provide an enzyme that efficiently degrades a sulfated fucoglucuronomannan derived from an alga of the order Fucales which is useful for glycotechnology and a method for producing the enzyme, as well as an oligosaccharide obtainable by allowing the enzyme to act on a sulfated fucoglucuronomannan and a method for producing the same. Another object of the present invention is to provide a fraction in which a sulfated fucoglucuronomannan is removed from a sulfated polysaccharide mixture fraction derived from a brown alga and a method for producing the same.

SUMMARY OF INVENTION

As a result of intensive studies, the present inventors have found that a bacterial strain belonging to genus *Fucophilus*, *Fucophilus fucoidanolyticus* strain SI-1234, produces a novel sulfated fucoglucuronomannan-degrading enzymes and a method for producing the enzyme. Furthermore, the present inventors have found that purity of a fucoidan fraction can be increased by degrading and removing a sulfated fucoglucuronomannan from a sulfated polysaccharide mixture fraction derived from a brown alga of the order Fucales utilizing the enzyme. Additionally, the present inventors have found that a novel sulfated fucoglucuronomannan oligosaccharide having a homogeneous structure can be produced from a sulfated polysaccharide mixture fraction derived from a brown alga of the order Fucales by utilizing the enzyme. Thus, the present invention has been completed.

The first aspect of the present invention relates to a sulfated fucoglucuronomannan oligosaccharide of general formula (I) or (II), or a salt thereof:

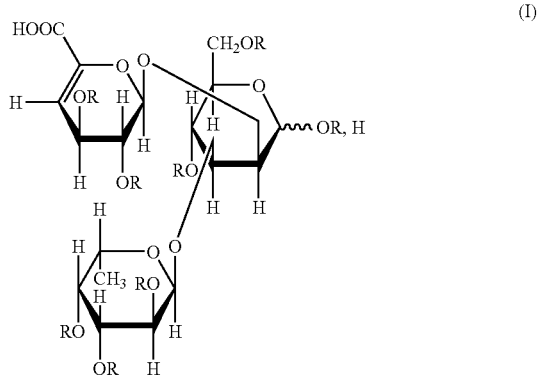

wherein R is H or $SO_3H$,

-continued

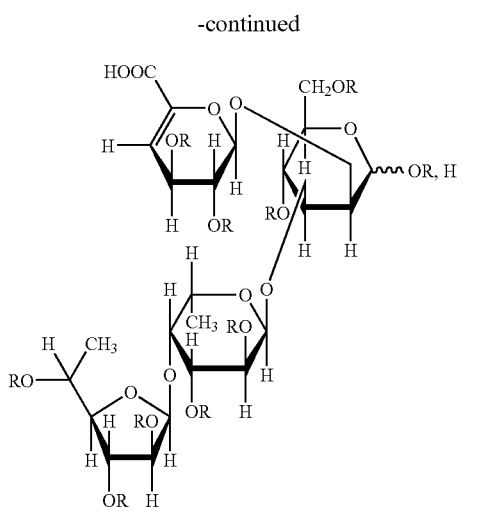
(II)

wherein R is H or SO$_3$H.

The second aspect of the present invention relates to a sulfated fucoglucuronomannan lyase having the following chemical and physical properties:

(I) acting on a sulfated fucoglucuronomannan derived from an alga of the order Fucales and cleaving an α-D-mannosyl bond eliminatively to generate an oligosaccharide having an unsaturated glucuronate group;

(II) having an optimal pH of about 6.5 to 8.0; and (III) having an optimal temperature of about 30 to 40° C.

The enzyme of the second aspect can be obtained according to a method comprising culturing a bacterium of the genus *Fucophilus* that is capable of producing the sulfated fucoglucuronomannan lyase and collecting said enzyme from the culture.

The saccharide or a salt thereof of the first aspect can be prepared according to a method for producing the saccharide comprising allowing the sulfated fucoglucuronomannan lyase of the second aspect to act on a sulfated fucoglucuronomannan fraction derived from an alga of the order Fucales.

The third aspect of the present invention relates to a fucoidan fraction which is obtainable according to a method comprising removing a sulfated fucoglucuronomannan converted into a smaller molecule by allowing the sulfated fucoglucuronomannan lyase of the second aspect to act on a sulfated polysaccharide mixture fraction derived from a brown alga.

The fucoidan fraction of the third aspect can be prepared according to a method for producing a fucoidan fraction comprising allowing the sulfated fucoglucuronomannan lyase of the second aspect to act on a sulfated polysaccharide mixture fraction derived from a brown alga; and collecting a fucoidan fraction.

The fourth aspect of the present invention relates to a reagent for glycotechnology which contains the sulfated fucoglucuronomannan lyase of the second aspect.

The fifth aspect of the present invention relates to a polysaccharide comprising a sulfated fucoglucuronomannan of general formula (X):

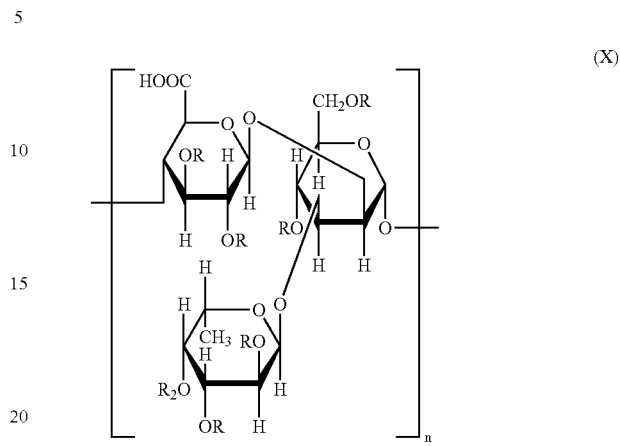
(X)

wherein R is H or SO$_3$H; R$_2$ is H, SO$_3$H or general formula (XI); and n is an integer of 1 or more:

(XI)

wherein R is H or SO$_3$H.

The sixth aspect of the present invention relates to a sulfated fucoglucuronomannan having the following chemical and physical properties, or a salt thereof:

(1) containing fucose, mannose and glucuronic acid as constituting saccharides; and (2) converted into a smaller molecule by the action of the sulfated fucoglucuronomannan lyase of the second aspect to generate at least one compound selected from a compound of general formula (I) or a compound of general formula (II):

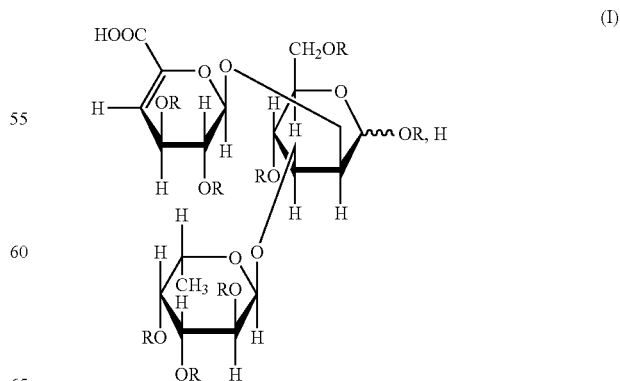
(I)

wherein R is H or SO₃H,

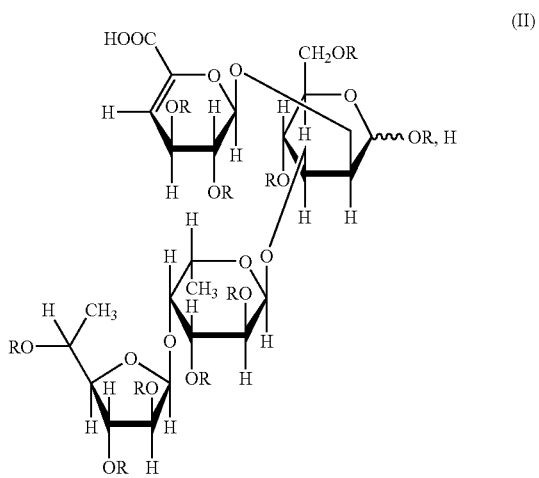

wherein R is H or SO₃H.

DETAILED DESCRIPTION OF THE INVENTION

Figure 1:
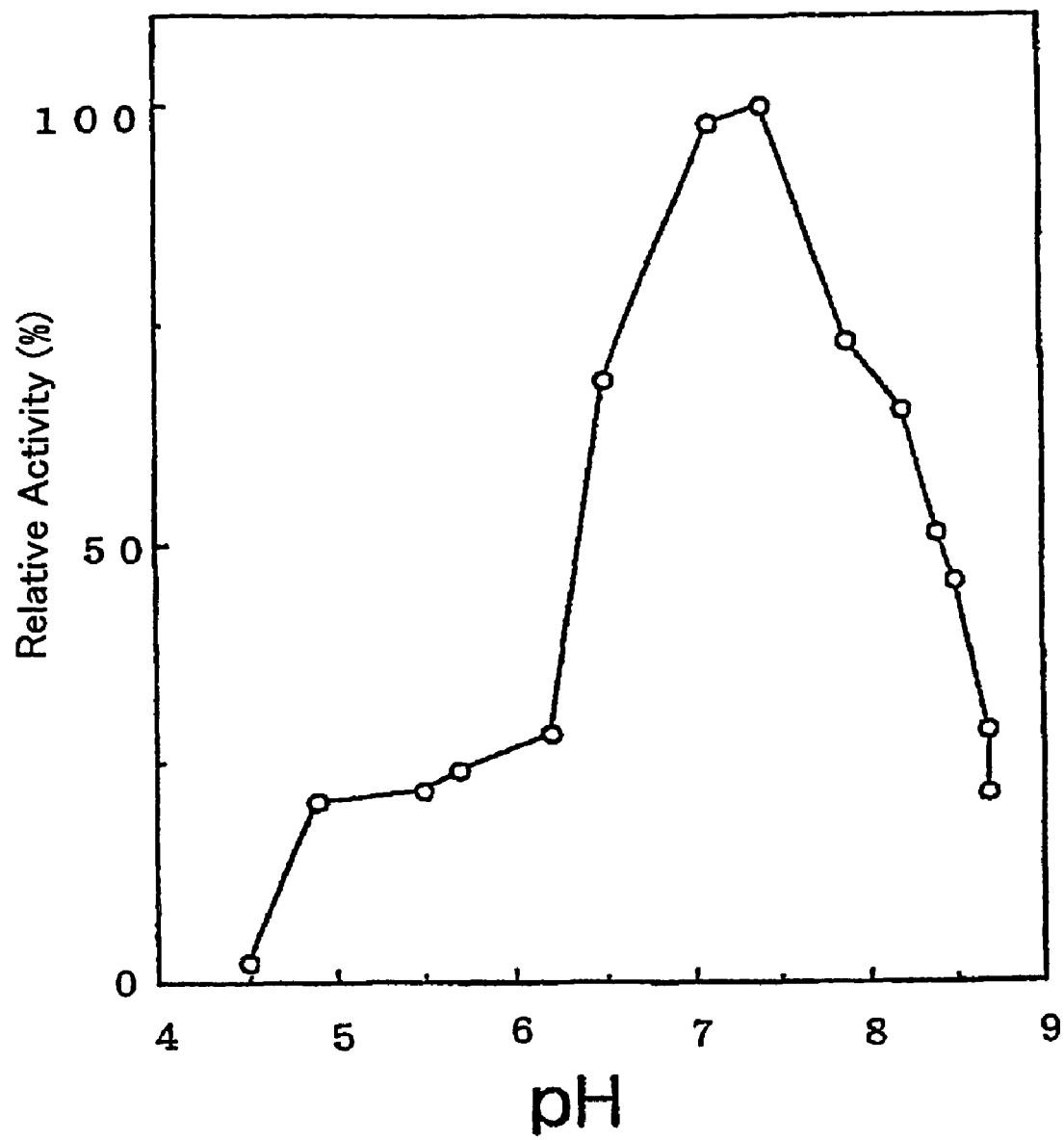
FIG. 1. a graph which illustrates the relationship between pH and the relative activity (%) of the sulfated fucoglucuronomannan lyase according to the present invention.

The present invention will be explained in detail.

As used herein, a sulfated fucoglucuronomannan refers to a sulfated polysaccharide contained in a brown alga which contains fucose, mannose and glucuronic acid as constituting saccharides. A substance having a chemical structure represented by the above-mentioned general formula (I) and/or (II) is obtained by allowing the sulfated fucoglucuronomannan lyase of the present invention to act on the sulfated fucoglucuronomannan. There is no specific limitation concerning the origin of the sulfated fucoglucuronomannan. For example, sulfated fucoglucuronomannans derived from brown algae of the order Fucales (e.g., *Fucus vesiculosus*, *Ascophyllum nodosum*) can be preferably used. As used herein, a sulfated fucoglucuronomannan fraction refers to a fraction that contains a sulfated fucoglucuronomannan.

As used herein, a sulfated fucoglucuronomannan lyase refers to an enzyme that acts on a sulfated fucoglucuronomannan derived from a brown alga and cleaves an α-D-mannosyl bond between mannose and glucuronic acid eliminatively to generate an oligosaccharide having an unsaturated glucuronate group.

As used herein, a sugar compound refers to a sulfated fucoglucuronomannan oligosaccharide, and includes a oligosaccharide obtainable by allowing the sulfated fucoglucuronomannan lyase of the present invention to act on a sulfated fucoglucuronomannan which has mannose at the reducing end.

When a sulfated fucoglucuronomannan is produced according to the present invention, water-soluble components contained in a brown alga are first extracted. In this case, it is preferable to carry out the extraction at pH 4–9 at a temperature of 100° C. or below in order to prevent conversion of the sulfated fucoglucuronomannan into smaller molecules. Furthermore, amino acids or small molecule pigments in the extract can be efficiently removed using ultrafiltration. Activated carbon treatment is effective for the removal of hydrophobic substances.

Thus, a sulfated polysaccharide mixture fraction derived from a brown alga can be obtained. This fraction can be used as a sulfated fucoglucuronomannan fraction, for example, as a substrate for the sulfated fucoglucuronomannan lyase of the present invention. A more highly pure sulfated fucoglucuronomannan can be obtained by separating the sulfated fucoglucuronomannan fraction using an anion exchange column. Either the sulfated polysaccharide mixture fraction or the sulfated fucoglucuronomannan purified using an anion exchange column may be used as a substrate for determining an activity upon purification of the sulfated fucoglucuronomannan lyase of the present invention. Also, it may be used as a raw material for producing the fucoidan fraction containing less molecular species and the sulfated fucoglucuronomannan oligosaccharide of the present invention.

Any bacterium that produces the sulfated fucoglucuronomannan lyase of the present invention may be used for the production without limitation. For example, *Fucophilus fucoidanolyticus* strain SI-1234 can be used.

*Fucophilus fucoidanolyticus* strain SI-1234 is a bacterium newly obtained by the present inventors by screening from a sea cucumber intestine. Its bacteriological properties are as follows.

a. Morphological Properties:
  (1) Coccus of 1.2 to 1.6 μm in diameter
  (2) Spore: no
  (3) Gram staining: negative b. Physiological Properties:
  (1) Growth temperature: 25° C.
  (2) Attitude to oxygen: aerobic
  (3) Catalase: positive
  (4) Oxidase: negative
  (5) Salt requirements:
  Growth in 0% salt medium: negative
  Growth in 1% salt medium: negative
  Growth in seawater medium: positive
  (6) Quinones: menaquinone 7
  (7) GC content of intracellular DNA: 52%
  (8) OF-test: not generating acid
  (9) Colony color: not generating characteristic colony pigment
  (10) Motility: negative
  (11) Gliding: negative
  (12) Flagellum: no This strain is classified into Group 4 (Gram-negative aerobic bacilli and cocci) according to the basic classification as described in Bergey's Manual of Determinative Bacteriology, Vol. 9 (1994). However, this strain is greatly different from bacteria belonging to Group 4 in that it has menaquinone 7 in its electron transport chain and the GC content is 52%.

The nucleotide sequence of the DNA encoding 16S rRNA (16S rDNA) of the strain was determined (SEQ ID NO:1) and compared its homologies to those of known bacteria. As a result, there was no known bacterium that exhibits high homology over the whole 16S rDNA region (about 1,500 bases). If the homology over the whole 16S rDNA sequence is 90% or less, two bacterial strains do not belong to the same genus. Accordingly, the present inventors concluded that this strain is a bacterium that does not belong to a known genus but belongs to a new genus, and designated as *Fucophilus fucoidanolyticus* strain SI-1234. The sulfated fucoglucuronomannan lyases of the present invention include a sulfated fucoglucuronomannan lyase obtained from a bacterium that is determined to belong to the same genus as *Fucophilus fucoidanolyticus* strain SI-1234 based on the nucleotide sequence of the 16S rDNA.

This strain is indicated as *Fucophilus fucoidanolyticus* strain SI-1234 and deposited under Budapest Treaty at International Patent Organism Depositary, National Institute of Advanced Science and Technology (AIST Tsukuba Central 6, 1—1, Higashi 1-Chome, Tsukuba, Ibaraki 305–8566, Japan) on Aug. 18, 1999 (date of transmission: Mar. 7, 2001) under accession number FERM BP-7495.

Any nutrient source can be added to a medium for culturing a microorganism producing the sulfated fucoglucuronomannan lyase of the present invention as long as the microorganism utilizes it to produce the enzymes. For example, a sulfated fucoglucuronomannan, an alga such as *Fucus vesiculosus* or *Ascophyllum nodosum*, alginic acid, laminaran, fucose, glucose, mannitol, glycerol, saccharose, maltose, starch and the like can be utilized as carbon sources. Yeast extract, peptone, casamino acid, corn steep liquor, meat extract, defatted soybean, ammonium sulfate, ammonium chloride, urea, uric acid and the like are suitable nitrogen sources. In addition, a chloride, a phosphate or a sulfate of sodium, potassium, magnesium, calcium, zinc or the like may be added. Generally, a microorganism obtained from seawater grows very well in seawater or commercially available artificial seawater.

The culture conditions are determined such that the productivity of the sulfated fucoglucuronomannan lyase of the present invention becomes maximal depending on the microorganism used, the composition of the medium or the like. Generally, the maximal productivity of the sulfated fucoglucuronomannan lyase of the present invention is achieved by culturing with aeration and stirring at a culture temperature of 15 to 30° C. at medium pH of 5 to 9 for 5 to 72 hours. The sulfated fucoglucuronomannan lyase of the present invention can be obtained from cells and a culture supernatant separated from each other by centrifugation after culturing.

A cell-free extract can be obtained by culturing *Fucophilus fucoidanolyticus* strain SI-1234 in an appropriate medium, collecting the cells, and disrupting the cells by a conventional means for cell disruption such as sonication. A purified enzyme preparation can be then obtained from the extract by a conventional means for purification. The sulfated fucoglucuronomannan lyase of the present invention in a purified form which is substantially free from other sulfated fucose-containing polysaccharide-degrading enzymes can be obtained by purification. For example, salting out, ion exchange column chromatography, hydrophobic column chromatography or gel filtration may be used for the purification.

Furthermore, a purification procedure similar to that for the purification of the intracellular enzyme can be used to purify the sulfated fucoglucuronomannan lyase of the present invention from the culture supernatant which also contains the enzyme in large quantities.

Figure 2:
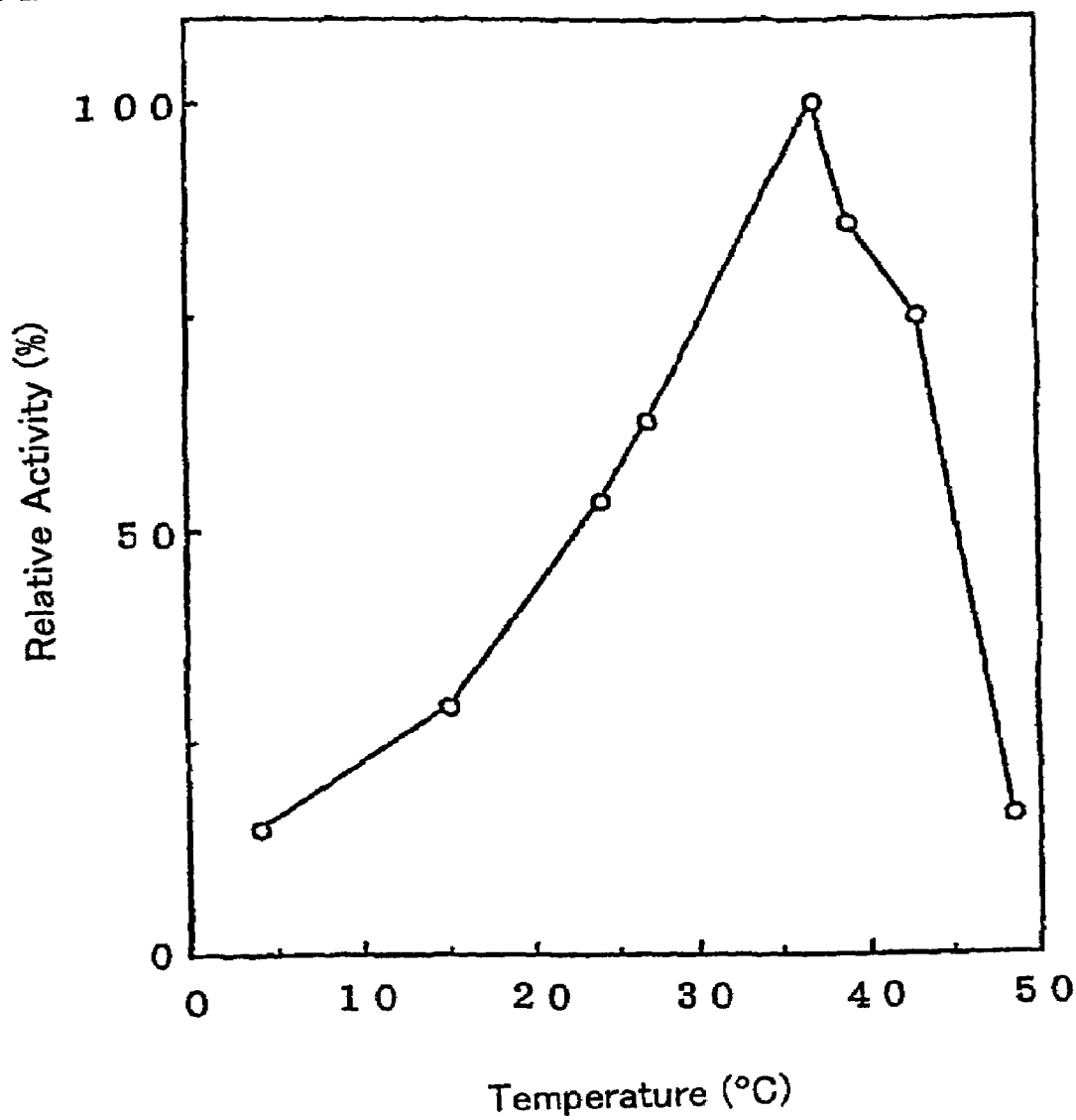
FIG. 2. a graph which illustrates the relationship between temperature (° C.) and the relative activity (%) of the sulfated fucoglucuronomannan lyase according to the present invention.

The chemical and physical properties of the sulfated fucoglucuronomannan lyase of the present invention are as follows:

(I) acting on a sulfated fucoglucuronomannan and cleaving an α-D-mannosyl bond eliminatively to generate an oligosaccharide having an unsaturated glucuronate group;

(II) having an optimal pH of about 6.5 to 8.0 (FIG. 1, a graph illustrating the relationship between the reaction pH and the relative activity of the enzyme of the present invention, in which the vertical axis represents the relative activity (%) and the horizontal axis represents the pH);

(III) having an optimal temperature of about 30 to 40° C. (FIG. 2, a graph which illustrates the relationship between the reaction temperature and the relative activity of the enzyme of the present invention, in which the vertical axis represents the relative activity (%) and the horizontal axis represents the temperature (° C.)); and (IV) having a molecular weight of about 500,000 to 600,000 as determined by gel filtration.

The sulfated fucoglucuronomannan lyase of the present invention can be identified by measuring an activity of degrading a sulfated fucoglucuronomannan. A cell-free extract from a producer strain or an enzyme solution obtained after purification using various column chromatographies may be used for the measurement.

*Fucophilus fucoidanolyticus* strain SI-1234 is a microorganism that utilizes a sulfated fucoglucuronomannan. It produces the sulfated fucoglucuronomannan lyase of the present invention inside and outside the cells for degrading the sulfated fucoglucuronomannan.

As used herein, a sulfated polysaccharide mixture fraction derived from a brown alga refers to a fraction that contains a fucoidan derived from a brown alga, i.e., a mixture of fucose-containing sulfated polysaccharides which is extracted from a brown alga.

According to the present invention, a fucoidan fraction containing less molecular species can be obtained by degrading a sulfated fucoglucuronomannan contained in a sulfated polysaccharide mixture fraction with an enzyme and removing it.

The fucoidan fraction containing less molecular species may be obtained by allowing the sulfated fucoglucuronomannan lyase to act on a sulfated polysaccharide mixture fraction extracted from a brown alga and removing a sulfated fucoglucuronomannan converted into smaller molecules, i.e., sulfated fucoglucuronomannan oligosaccharides. For example, ultrafiltration, gel filtration, anion exchange column treatment or the like may be used for the purification. Optionally, desalting, lyophilization or the like may be carried out.

For example, a sulfated polysaccharide mixture fraction derived from an alga of the order Fucales contains several kinds of sulfated polysaccharides such as a sulfated fucoglucuronomannan in addition to a sulfated fucan. A fucoidan fraction containing less molecular species can be prepared by degrading and removing the sulfated fucoglucuronomannan using a sulfated fucoglucuronomannan lyase. The fucoidan fraction containing less molecular species and a sulfated fucoglucuronomannan oligosaccharide generated by degrading the sulfated fucoglucuronomannan are useful as reagents for glycotechnology.

Upon preparation of the fucoidan fraction containing less molecular species of the present invention, a sulfated polysaccharide mixture fraction derived from a brown alga may be dissolved according to a conventional method. The sulfated polysaccharide mixture fraction may be dissolved in the solution at the maximal concentration. However, the concentration may be usually selected taking its operationality, the amount of the sulfated fucoglucuronomannan lyase of the present invention to be used for the degradation and the like into consideration. The solvent for the sulfated polysaccharide mixture fraction may be selected from water, buffers and the like depending on the objects. Usually, the pH of the solution is nearly neutral. The enzymatic reaction is usually carried out at about −30° C. Optionally, the fucoidan fraction containing less molecular species may be further purified using ion exchange resin treatment, ultrafiltration or the like, or they may be desalted, sterilized or lyophilized.

A substance contained in the fucoidan fraction containing less molecular species of the present invention has a sulfate group and/or a carboxyl group in its molecule. Such groups react with various bases to form salts. Since the substance contained in the fucoidan fraction containing less molecular species of the present invention is stable in a form of salt, it is usually provided, for example, in a form of salt with sodium, potassium and/or calcium one can convert the salt into the substance contained in the fucoidan fraction containing less molecular species of the present invention in a free form by utilizing a cation exchange resin such as Dowex 50W. Optionally, the salts may be subjected to conventional salt exchange for other various desirable salts.

A substance contained in the fucoidan fraction containing less molecular species of the present invention can be converted into a pharmaceutically acceptable salt. Examples of the salts include salts with alkaline metals such as sodium and potassium, salts with alkaline earth metals such as calcium and magnesium, as well as salts with ammonium and zinc.

The sulfated fucoglucuronomannan oligosaccharide of the present invention can be prepared by allowing the sulfated fucoglucuronomannan lyase of the present invention to act on a sulfated fucoglucuronomannan or a sulfated fucoglucuronomannan-containing material. For example, a partially purified preparation of a sulfated fucoglucuronomannan, a sulfated polysaccharide mixture fraction derived from a brown alga, an aqueous solvent extract of a brown alga, or a brown alga itself can be preferably used as the sulfated fucoglucuronomannan-containing material Upon preparation of the sulfated fucoglucuronomannan oligosaccharide of the present invention, a sulfated fucoglucuronomannan or a sulfated fucoglucuronomannan-containing material may be dissolved according to a conventional method. The sulfated fucoglucuronomannan or the sulfated fucoglucuronomannan-containing material may be dissolved in the solution at the maximal concentration. However, the concentration may be usually selected taking its operationality and the amount of the sulfated fucoglucuronomannan lyase of the present invention to be used for the reaction into consideration. The solvent for the sulfated fucoglucuronomannan may be selected from water, buffers and the like depending on the objects. Usually, the pH of the solution is nearly neutral. The enzymatic reaction is usually carried out at about 30° C. The molecular weight of the sulfated fucoglucuronomannan oligosaccharide can be controlled by adjusting the amount of the sulfated fucoglucuronomannan lyase of the present invention used for the reaction, the composition of the reaction mixture, the reaction time or the like. The sulfated fucoglucuronomannan oligosaccharide of the present invention having more homogeneous molecular weight can be prepared by fractionating the sulfated fucoglucuronomannan oligosaccharide of the present invention obtained as described above using molecular weight fractionation or anion exchange column. A conventional means for molecular weight fractionation such as gel filtration or ultrafiltration may be used. Optionally, the smaller molecules may be subjected to further purification procedure using ion exchange resin treatment, activated carbon treatment or the like, or they may be desalted, sterilized or lyophilized. The sulfated fucoglucuronomannan oligosaccharide of the present invention having a structure so homogeneous that one can determine the structure by NMR analysis as described below can be obtained by such a procedure. Examples of the sulfated fucoglucuronomannan oligosaccharides include compounds represented by formulas (I) and (II) below. Although it is not intended to limit the present invention, at least one of the Rs is preferably $SO_3H$ in formulas (I) and (II).

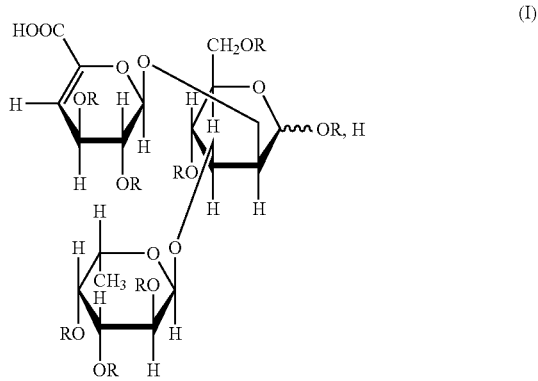

(I)

wherein R is H or SO$_3$H,

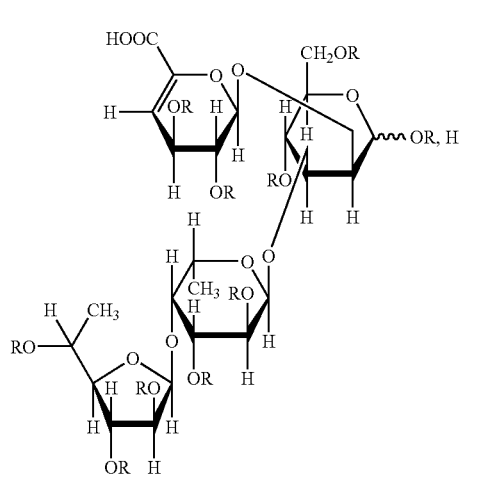

(II)

wherein R is H or SO$_3$H.

The sulfated fucoglucuronomannan oligosaccharide of the present invention has a sulfate group and a carboxyl group in its molecule. Such groups react with various bases to form salts. Since the sulfated fucoglucuronomannan oligosaccharide of the present invention is stable in a form of salt, it is usually provided, for example, in a form of salt with sodium, potassium and/or calcium. One can convert the salt into the sulfated fucoglucuronomannan oligosaccharide of the present invention in a free form by utilizing a cation exchange resin such as Dowex 50W. Optionally, the salts may be subjected to conventional salt exchange for other various desirable salts.

The sulfated fucoglucuronomannan oligosaccharide of the present invention can be converted into a pharmaceutically acceptable salt. Examples of the salts include salts with alkaline metals such as sodium and potassium, salts with alkaline earth metals such as calcium and magnesium, as well as salts with ammonium and zinc.

The sulfated fucoglucuronomannan lyase of the present invention converts a sulfated fucoglucuronomannan into smaller molecules. So, it can be used for the structural analysis of the sulfated fucoglucuronomannan. The sulfated fucoglucuronomannan oligosaccharide of the present invention can be used as a reagent for glycotechnology. For example, a 2-aminopyridine (PA)-labeled oligosaccharide prepared by subjecting the oligosaccharide to PA-labeling according to the method as described in JP-B 5-65108 can be used as a substrate for a fucofuranosidase or a 5-sulfated fucofuranosidase. Thus, a substance very useful as a reagent for glycotechnology can be provided.

The sulfated fucoglucuronomannan of the present invention is a polysaccharide having a structure in which fucose side chains are extended from mannose in a sugar chain composed of glucuronic acid and mannose alternately bound to each other. The polysaccharides are often polymerized via a crosslinkage of a divalent cation or the like. Although it is not intended to limit the present invention, the molecular weights after cleaving the crosslinkages range from 5,000 to 2,000,000, preferably from 10,000 to 1,000,000. Although it is not intended to limit the present invention, one represented by general formula (X) exemplifies the sulfated fucoglucuronomannan. In general formula (X), n is an integer of 1 or more, preferably 5 to 2000, more preferably 10 to 1000.

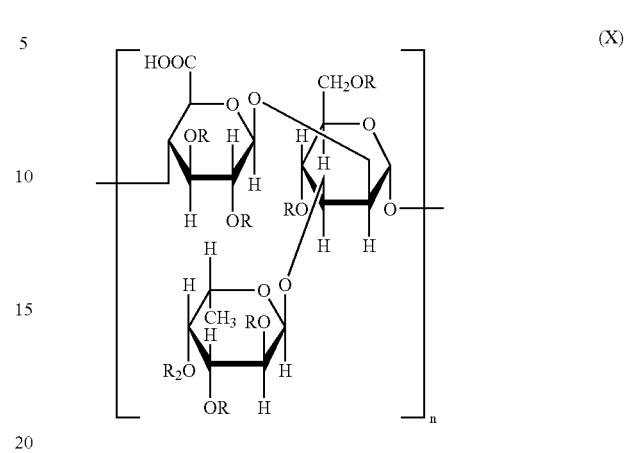

(X)

wherein R is H or SO$_3$H; R$_2$ is H, SO$_3$H or general formula (XI); and n is an integer of 1 or more:

(XI)

wherein R is H or SO$_3$H.

EXAMPLES

The following examples further illustrate the present invention in detail but are not to be construed to limit the scope thereof.

Referential Example 1

Preparation of Sulfated Polysaccharide Mixture Fraction Derived from *Fucus vesiculosus*

Dried *Fucus vesiculosus* alga was ground. 1 kg of the ground alga was suspended in 10 L of 80% ethanol. The suspension was stirred at 25° C. for 3 hours, filtered, and then washed to obtain a residue. The residue was suspended in 30 L of 30 mM phosphate buffer (pH 6.5) containing 100 mM sodium chloride. The suspension was treated at 95° C. for 2 hours and then cooled to 30° C. 100 g of activated carbon, 3000 U of alginate lyase (Nagase Biochemicals) and 3.75 L of ethanol were added thereto. The mixture was stirred for 24 hours, and then centrifuged to obtain a supernatant. The supernatant was concentrated to 4 L using an ultrafiltration device equipped with hollow fibers with exclusion molecular weight of 100,000. The solvent was exchanged for 100 mM sodium chloride. The solution was cooled to 5° C. The pH was adjusted to 2.0 with 0.5 N hydrochloric acid. The formed precipitate was removed by centrifugation to obtain a supernatant. The pH of the supernatant was adjusted to 8.0 with 1 N sodium hydroxide. The solution was concentrated to 2 L using the above-mentioned ultrafiltration device and the solvent was exchanged for 20 mM sodium chloride. Insoluble substances were removed by centrifugation. The solution was lyophilized to obtain 80 g of a sulfated polysaccharide mixture fraction derived from *Fucus vesiculosus*.

Referential Example 2

Preparation of Sulfated Polysaccharide Mixture Fraction Derived from *Ascophyllum nodosum*

100 g of a sulfated polysaccharide mixture fraction derived from *Ascophyllum nodosum* was obtained from 1 kg of commercially available *Ascophyllum nodosum* powder according to the method as described in Referential Example 1.

Referential Example 3

Preparation of Sulfated Polysaccharide Mixture Fraction Derived from *Kjellmaniella crassifolia* Miyabe Commercially available *Kjellmaniella crassifolia* Miyabe was disrupted using a cutter mill (Masuko Sangyo) to prepare chips. 38 g of a sulfated polysaccharide mixture fraction derived from *Kjellmaniella crassifolia* Miyabe was obtained from 1 kg of the chips according to the method as described in Referential Example 1.

Referential Example 4

Preparation of Sulfated Fucoglucuronomannan Fraction Derived from *Fucus vesiculosus*

7 g of the sulfated polysaccharide mixture fraction derived from *Fucus vesiculosus* as described in Referential Example 1 was dissolved in 700 ml of 20 mM imidazole-hydrochloride buffer (pH 6.0) containing 100 mM sodium chloride. The solution was loaded onto a 5-L DEAE-Cellulofine A-800 equilibrated with the same buffer. The sample was run, the column was washed with 10 L of the same buffer, and elution was carried out with a gradient of 100 to 1600 mM sodium chloride to collect fractions (500 ml). The total sugar content and the total uronic acid content of each fraction were measured according to the phenol-sulfuric acid method and the carbazole-sulfuric acid method, respectively. A fraction eluted with 200–700 mM sodium chloride was concentrated by ultrafiltration (exclusion molecular weight of 100,000), desalted and lyophilized to obtain 1.3 g of a sulfated fucoglucuronomannan fraction derived from *Fucus vesiculosus*.

Referential Example 5

Preparation of Sulfated Fucoglucuronomannan Fraction Derived from *Ascophyllum nodosum*

1.1 g of a sulfated fucoglucuronomannan fraction derived from *Ascophyllum nodosum* was obtained from 7 g of the sulfated polysaccharide mixture fraction derived from *Ascophyllum nodosum* as described in Referential Example 2 according to the method as described in Referential Example 4.

Referential Example 6

Preparation of Sulfated Fucoglucuronomannan Fraction Derived from *Kjellmaniella crassifolia* Miyabe 7 g of the sulfated polysaccharide mixture fraction derived from *Kjellmaniella crassifolia* Miyabe as described in Referential Example 3 was dissolved in 700 ml of 20 mM imidazole-hydrochloride buffer (pH 8.0) containing 150 mM sodium chloride. The solution was loaded onto a 5-L DEAE-Cellulofine A-800 equilibrated with the same buffer. The sample was run, the column was washed with 10 L of the same buffer, and elution was carried out with a gradient of 150 to 1950 mM sodium chloride to collect fractions (500 ml). The total sugar content and the total uronic acid content of each eluted fraction were measured according to the phenol-sulfuric acid method and the carbazole-sulfuric acid method, respectively. A fraction eluted with 350–490 mM sodium chloride was concentrated by ultrafiltration (exclusion molecular weight of 100,000), desalted and lyophilized to obtain 1.32 g of a sulfated fucoglucuronomannan fraction derived from *Kjellmaniella crassifolia* Miyabe.

Referential Example 7

Method for Measuring Sulfated Fucoglucuronomannan Lyase Activity

When the sulfated fucoglucuronomannan lyase of the present invention is allowed to act on a sulfated fucoglucuronomannan, an oligosaccharide having an unsaturated glucuronate group is generated, resulting in increased absorbance at 232 nm. A sulfated fucoglucuronomannan lyase activity was measured utilizing it as follows. The sulfated fucoglucuronomannan lyase of the present invention acts on sulfated fucoglucuronomannans derived from *Fucus vesiculosus* and *Ascophyllum nodosum*. It also acts on a sulfated fucoglucuronomannan derived from *Kjellmaniella crassifolia* Miyabe. Then, a sulfated fucoglucuronomannan derived from *Kjellmaniella crassifolia* Miyabe was used as a substrate for the measurements of activities because it can be readily prepared.

Briefly, 50 μl of 2.5% solution of the sulfated fucoglucuronomannan fraction derived from *Kjellmaniella crassifolia* Miyabe as described in Referential Example 6, 50 μl of 100 mM phosphate buffer (pH 7.5), 10 μl of 4 M sodium chloride and 10 μl of the sulfated fucoglucuronomannan lyase of the present invention were mixed together. After reacting at 37° C. for 3 hours, 105 μl of the reaction mixture was diluted with 2 ml of cold water. The absorbance at 232 nm was measured. As controls, a reaction mixture obtained by a reaction in which the solvent used for the enzyme solution was used in place of the sulfated fucoglucuronomannan lyase of the present invention, and a reaction mixture obtained by a reaction in which water was used in place of the sulfated fucoglucuronomannan fraction were similarly analyzed.

One unit of a sulfated fucoglucuronomannan lyase activity is defined as an amount of an enzyme that generates 1 μmol of an unsaturated glucuronate group in 1 minute in the above-mentioned reaction system. The activity of the enzyme was calculated according to the following formula:

$$A_{232} \times 2.105/5.5/180/0.01 = U/ml$$

$A_{232}$: Increased absorbance at 232 nm;

2.105: Volume of sample subjected to absorbance measurement (ml);

5.5: Molecular extinction coefficient (/mM) of unsaturated glucuronate group;

180: Reaction time (minutes);

0.01: Volume of enzyme solution (ml).

The amount of protein was determined by measuring the absorbance at 280 nm of the enzyme solution. The calculation was carried out assuming the absorbance of a solution containing a protein at a concentration of 1 mg/ml as 1.0.

Example 1

Preparation of Sulfated Fucoglucuronomannan Lyase

*Fucophilus fucoidanolyticus* strain SI-1234 was inoculated into 600 ml of a medium consisting of artificial seawater (Jamarin Laboratory) (pH 8.0) containing the sulfated polysaccharide mixture fraction derived from *Fucus vesiculosus* as described in Referential Example 1 and peptone at concentrations of 0.2% and 1%, respectively, which had been autoclaved at 120° C. for 20 minutes, and cultured at 24° C. for 72 hours to prepare a seed culture. A 30-L jar fermentor containing 20 L of a medium consisting of artificial seawater (Jamarin Laboratory) (pH 8.0) containing the sulfated polysaccharide mixture fraction derived from *Fucus vesiculosus* as described in Referential Example 1 and peptone at concentrations of 0.2% and 1%, respectively, as well as an antifoaming agent (KM70, Shin-Etsu Chemical) was treated at 120° C. for 20 minutes. The seed culture was inoculated into the medium and cultured at 125 rpm at 24° C. for 48 hours. After cultivation, the culture was centrifuged to obtain cells and a supernatant.

The cells were suspended in 600 ml of 20 mM imidazole-hydrochloride buffer (pH 7.0) containing 400 mM sodium chloride and 10 mM calcium chloride, sonicated and centrifuged to obtain a supernatant. The supernatant was adequately dialyzed against the same buffer and centrifuged to obtain a supernatant as a crude enzyme solution of the sulfated fucoglucuronomannan lyase of the present invention.

Sulfated fucoglucuronomannan lyase activities contained in the culture supernatant and the crude enzyme solution were measured. As a result, 1 mU and 2 mU of the activities were detected in the culture supernatant corresponding to 1 ml of the medium and the cell extract corresponding to 1 ml of the medium, respectively.

Example 2

Preparation of Sulfated Fucoglucuronomannan Oligosaccharides Using Crude Enzyme Solution of Sulfated Fucoglucuronomannan Lyase, as well as Purification and Structural Analyses Thereof (1).

(1) Preparation

The sulfated fucoglucuronomannan oligosaccharides of the present invention were prepared by allowing the crude enzyme solution as described in Example 1 to act on the sulfated polysaccharide mixture fraction derived from *Fucus vesiculosus* as described in Referential Example 1. Briefly, 5 g of the sulfated polysaccharide fraction derived from *Fucus vesiculosus* was dissolved in 500 ml of 25 mM imidazole-hydrochloride buffer (pH 7.0) containing 300 mM sodium chloride and 50 mM calcium chloride. 50 ml of the crude enzyme solution as described in Example 1 was then added thereto. The mixture was reacted at 25° C. for 4 days. A supernatant obtained by centrifuging the reaction mixture was subjected to an ultrafiltration device equipped with hollow fibers with exclusion molecular weight of 10,000 to collect a fraction of oligosaccharides having molecular weight of 10,000 or less. This fraction was designated as a sulfated fucoglucuronomannan enzymatic digestion product fraction 1.

(2). Purification

The sulfated fucoglucuronomannan enzymatic digestion product fraction 1 obtained in Example 2-(1) was desalted using a desalting apparatus (Micro Acilyzer G3, Asahi Kasei). Imidazole and sodium chloride were added thereto at final concentrations of 10 mM and 10 mM, respectively. The resulting mixture was loaded onto a 1-L DEAE-Cellulofine A-800 column equilibrated with 10 mm imidazole-hydrochloride buffer (pH 6.0) containing 10 mM sodium chloride. After washing with 2 L of the same buffer, elution and collection were then carried out with a gradient of 10 to 1200 mM sodium chloride. The absorbance at 232 nm was measured for each fraction. The total sugar content and the total uronic acid content of each fraction were measured according to the phenol-sulfuric acid method and the carbazole-sulfuric acid method, respectively. As a result, the fractions of the latter half of washing and the fractions eluted with 360 mM sodium chloride formed peaks for which the absorbance at 232 nm, the total sugar content and the total uronic acid content were proportional to each other. The fractions in each peak were pooled and the pools were designated as oligosaccharide fractions 1-(1) and 1-(2), respectively.

Water was added to the oligosaccharide fraction 1-(1) to make the electric conductivity equivalent to that of 10 mM imidazole-hydrochloride buffer (pH 6.0) containing 5 mM sodium chloride. The mixture was loaded onto a 30-ml DEAE-Cellulofine A-800 column equilibrated with 10 mM imidazole-hydrochloride buffer (pH 6.0) containing 5 mm sodium chloride. The column was washed with 60 ml of the same buffer. The flow-through fraction was collected, concentrated to 2.8 ml using an evaporator, loaded onto a Cellulofine GCL-25 column (2×32 cm) equilibrated with 10% ethanol, eluted with 10% ethanol for desalting and then dried. Thus, 1.6 mg of the sulfated fucoglucuronomannan oligosaccharide 1-(1) of the present invention was obtained.

Water was added to the oligosaccharide fraction 1-(2) to make the electric conductivity equivalent to that of 10 mM imidazole-hydrochloride buffer (pH 6.0) containing 200 mM sodium chloride. The mixture was loaded onto a 20-ml DEAE-Cellulofine A-800 column equilibrated with 10 mM imidazole-hydrochloride buffer (pH 6.0) containing 200 mM sodium chloride. The column was washed with 40 ml of the same buffer. Elution was carried out with a gradient of 200–500 mM sodium chloride. A fraction eluted with 240–320 mM sodium chloride was collected, concentrated to 1.0 ml using an evaporator, loaded onto a Cellulofine GCL-25 column (2×32 cm) equilibrated with 10% ethanol, eluted with 10% ethanol for desalting and then dried. Thus, 6.4 mg of the sulfated fucoglucuronomannan oligosaccharide 1-(2) of the present invention was obtained.

(3) Structural Analyses

The sulfated fucoglucuronomannan oligosaccharides 1-(1) and 1-(2) of the present invention obtained in Example 2-(2) were subjected to analyses of saccharides at the reducing ends and saccharide compositions after fluorescence labeling with 2-aminopyridine. As a result, the saccharide at the reducing end for each of the sulfated fucoglucuronomannan oligosaccharides 1-(1) and 1-(2) of the present invention was determined to be mannose. Regarding the neutral sugar composition, each oligosaccharide consisted of fucose and mannose. Next, determination of the sulfuric acid content (measured according to the turbidimetric method using barium chloride) and the uronic acid content (measured according to the carbazole-sulfuric acid method), mass spectrometric analysis using a mass spectrometer API-III, (Perkin-Elmer Sciex) and NMR analysis using a nuclear magnetic resonance apparatus JNM-α500 (Nippon Denshi) were carried out. Samples to be analyzed were subjected to structural analyses after exchange for heavy water according to a conventional method. Bonds of constituting saccharides were analyzed using the HMBC method, a method for $^1$H-detection of heteronuclei. The DQF-COSY method and the HOHAHA method were used for assignment in $^1$H-NMR.

Physical properties of the sulfated fucoglucuronomannan-oligosaccharides-1-(1) and 1-(2) of the present invention are shown below.

Figure 3:
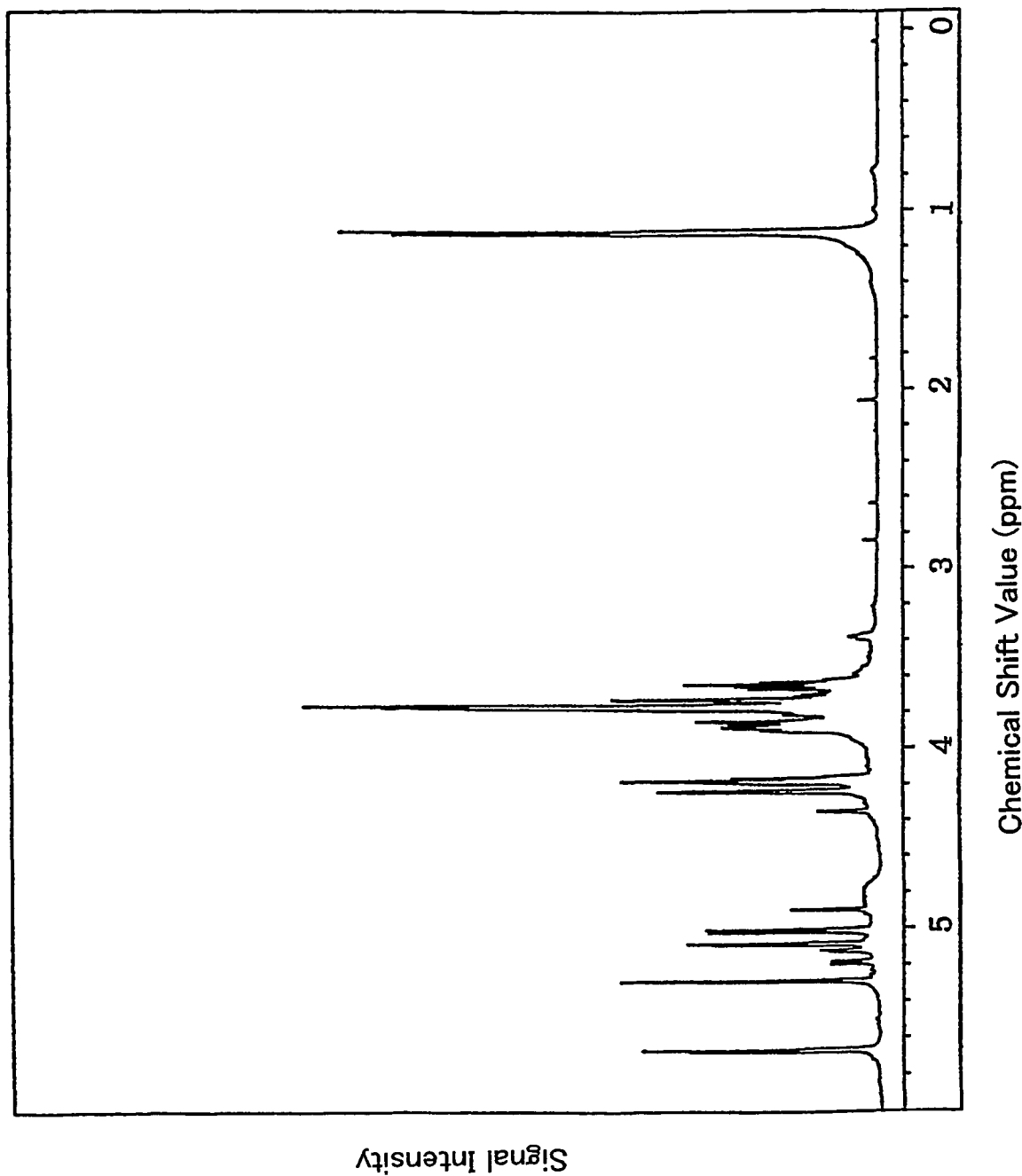
FIG. 3. a figure which illustrates the $^1$H-NMR spectrum of the sulfated fucoglucuronomannan oligosaccharide 1-(1) according to the present invention.
Figure 4:
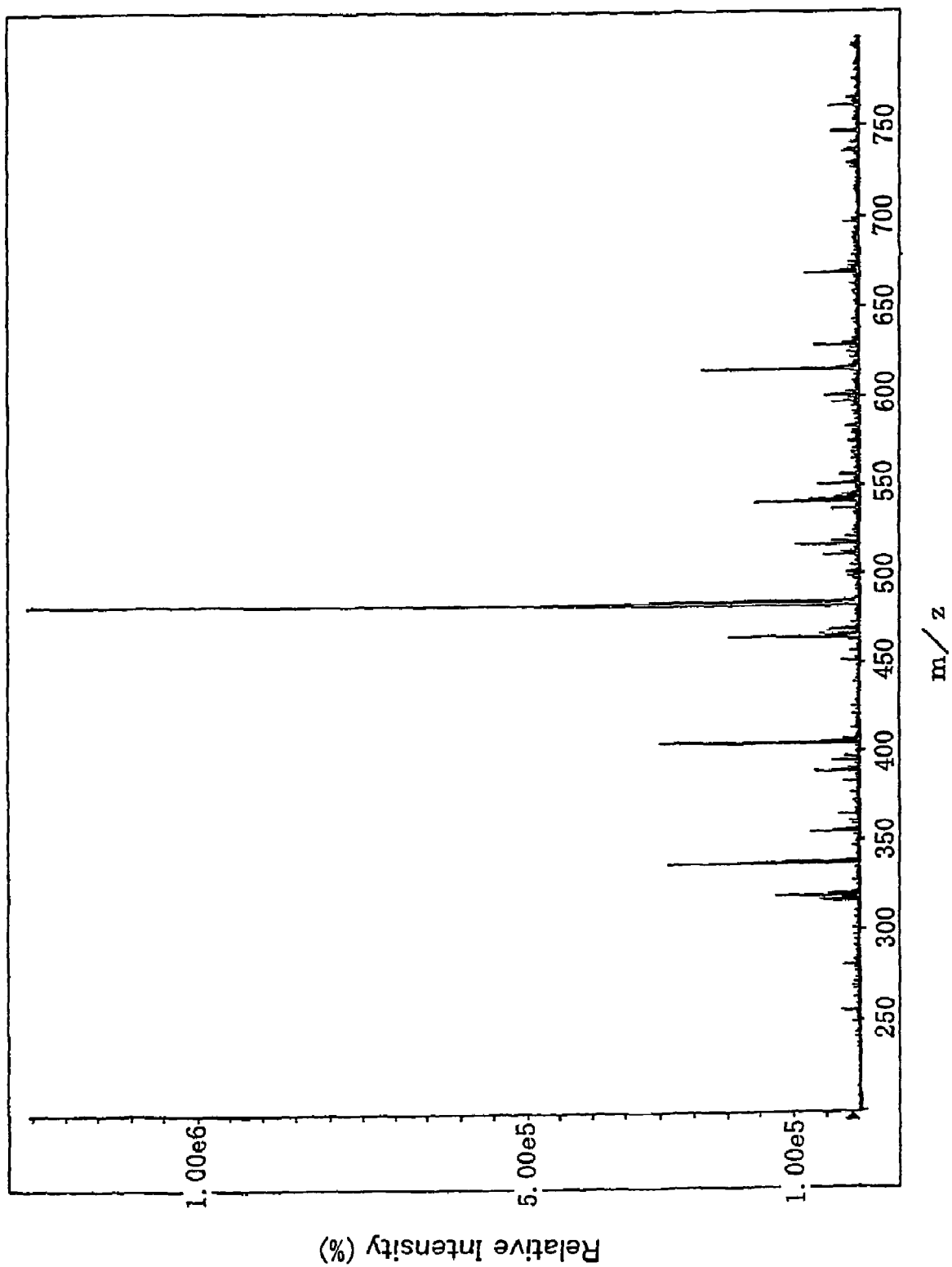
FIG. 4. a figure which illustrates the mass spectrum of the sulfated fucoglucuronomannan oligosaccharide 1-(1) according to the present invention.

(a) Physical Properties of the Sulfated Fucoglucuronomannan Oligosaccharide 1-(1) of the Present Invention The results for mass spectrometric analysis and assignment in NMR analyses are shown below. The $^1$H-NMR spectrum and mass spectrum are illustrated in FIGS. 3 and 4, respectively. In FIG. 3, the vertical axis represents the signal intensity and the horizontal axis represents the chemical shift value (ppm). In FIG. 4, the vertical axis represents the relative intensity and the horizontal axis represents the m/z value.

Molecular weight: 484

MS m/z 483.3 [M−H$^+$]$^-$

The results of $^1$H-NMR analyses are shown in Table 1.

TABLE 1

|  | Chemical shift value (ppm) $^1$H-NMR Chemical shift value, multiplicity, coupling constant |
|---|---|
| F1-1 | 5.08, d, 4.0 |
| F1-2 | 3.78, m |
| F1-3 | 3.86, dd, 3.5, 10.0 |
| F1-4 | 3.73, m |
| F1-5 | 4.18, m |
| F1-6 | 1.12, d, 7.0 |
| M-1 | 5.29, d, 1.5 |
| M-2 | 4.24, dd, 1.5, 3.0 |
| M-3 | 3.90, dd, 3.0, 9.0 |
| M-4 | 3.78, m |
| M-5 | 3.78, m |
| M-6 | 3.78, m |
| ΔGA-1 | 5.02, d, 7.0 |
| ΔGA-2 | 3.65, t, 7.0 |
| ΔGA-3 | 4.18, m |
| ΔGA-4 | 5.68, d, 3.5 |
| ΔGA-5 | — |
| ΔGA-6 | — |

Saccharide composition: L-fucose:D-mannose:unsaturated glucuronic acid=1:1:1

Sulfate group: None

The numbers for peak assignment in $^1$H-NMR are as indicated in formula (III) below:

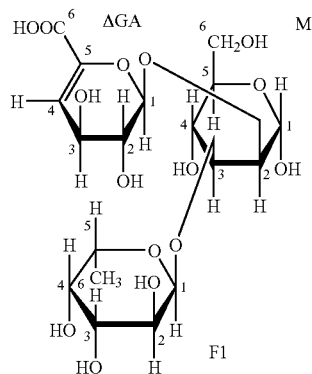

(III)

Figure 5:
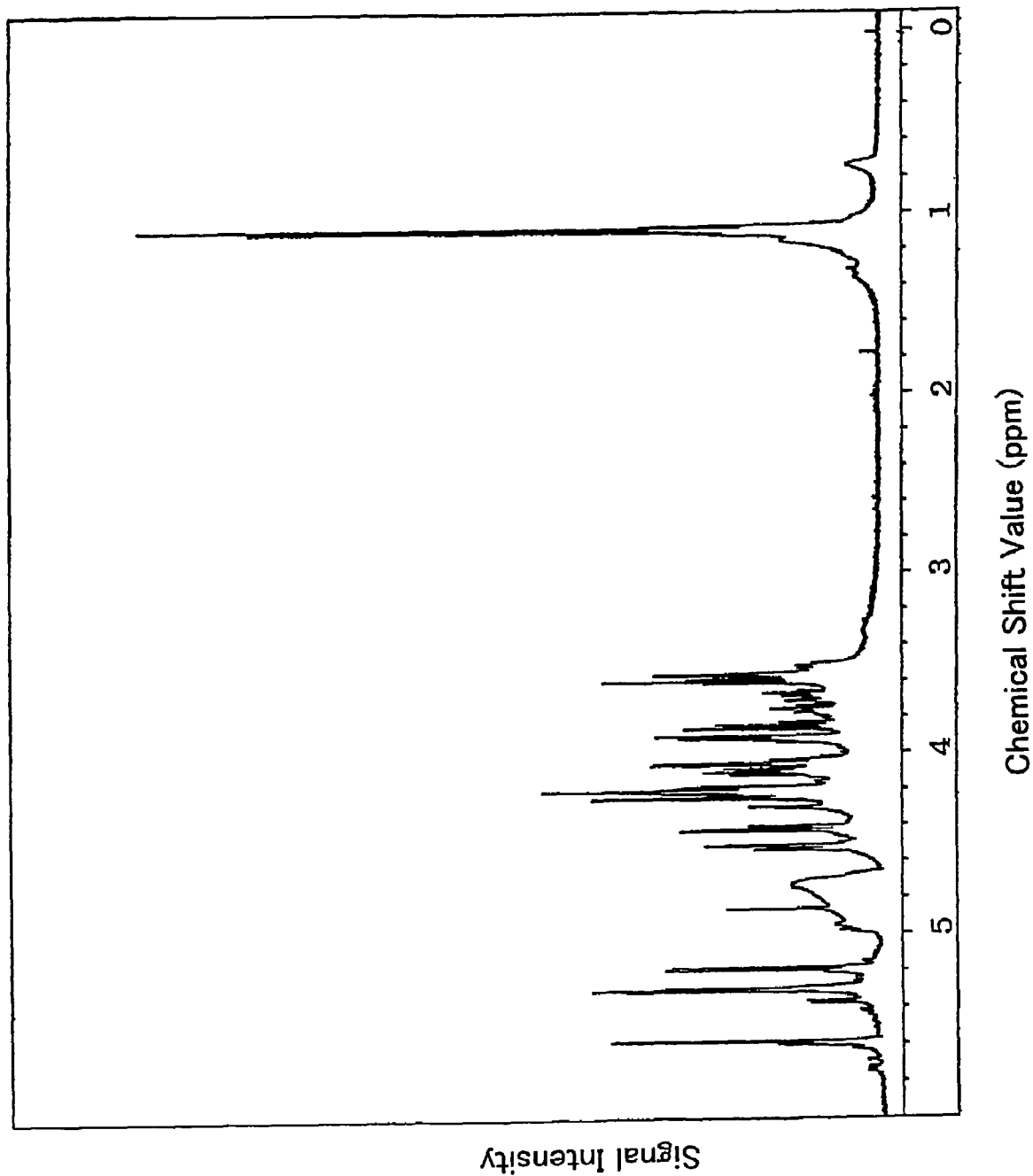
FIG. 5. a figure which illustrates the $^1$H-NMR spectrum of the sulfated fucoglucuronomannan oligosaccharide 1-(2) according to the present invention.
Figure 6:
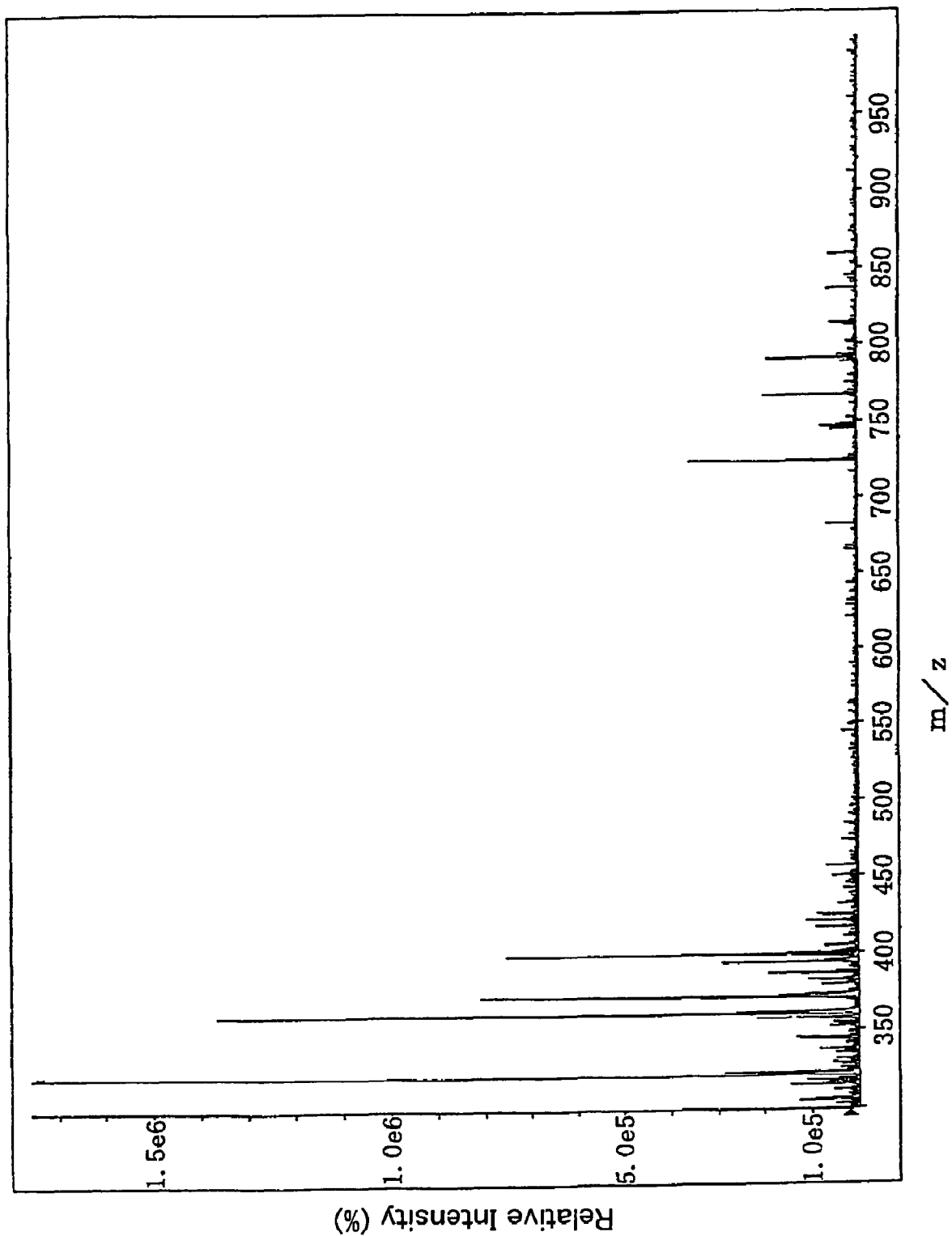
FIG. 6. a figure which illustrates the mass spectrum of the sulfated fucoglucuronomannan oligosaccharide 1-(2) according to the present invention.

(b) Physical Properties of the Sulfated Fucoglucuronomannan Oligosaccharide 1-(2) of the Present Invention The results for mass spectrometric analysis and assignment in NMR analyses are shown below. The $^1$H-NMR spectrum and mass spectrum are illustrated in FIGS. 5 and 6, respectively. In FIG. 5, the vertical axis represents the signal intensity and the horizontal axis represents the chemical shift value (ppm). In FIG. 6, the vertical axis represents the relative intensity and the horizontal axis represents the m/z value.

Molecular weight: 724

MS m/z 723.1 [M−H$^+$]$^-$, 766.7 [M+2Na$^+$−3H$^+$]$^-$, 790.5 [M+3NA$^+$−4H$^+$]$^-$, 360.9 [M−2H$^+$]$^{2-}$, 372.0 [M+Na$^+$−3H$^+$]$^{2-}$

The results of $^1$H-NMR analyses are shown in Table 2.

TABLE 2

|  | Chemical shift value (ppm) $^1$H-NMR Chemical shift value, multiplicity, coupling constant |
|---|---|
| F1-1 | 5.30, d, 4.0 |
| F1-2 | 4.42, dd, 4.0, 10.0 |
| F1-3 | 4.52, dd, 3.0, 10.0 |
| F1-4 | 4.06, d, 3.0 |
| F1-5 | 4.13, m |
| F1-6 | 1.09, d, 6.5 |
| M-1 | 5.31, d, 2.5 |
| M-2 | 4.25, m |
| M-3 | 3.91, m |
| M-4 | 3.85, t, 9.0 |
| M-5 | 3.93, m |
| M-6 | 4.10, dd, 6.0, 11.0 |
|  | 4.22, m |
| ΔGA-1 | 5.18, d, 7.0 |
| ΔGA-2 | 3.60, t, 7.0 |
| ΔGA-3 | 4.20, dd, 3.0, 7.0 |
| ΔGA-4 | 5.59, d, 3.0 |
| ΔGA-5 | — |
| ΔGA-6 | — |

Saccharide composition: L-fucose:D-mannose:unsaturated glucuronic acid=1:1:1

Sulfate group: 3 molecules

The numbers for peak assignment in $^1$H-NMR are as indicated in formula (IV) below:

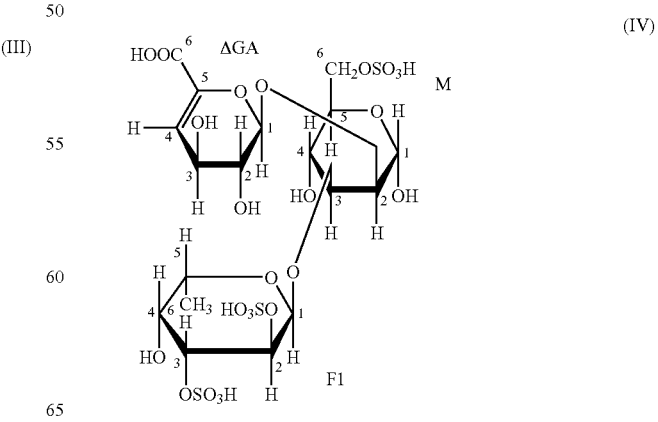

(IV)

Example 3

Preparation of Sulfated Fucoglucuronomannan Oligosaccharides Using Crude Enzyme Solution of Sulfated Fucoglucuronomannan Lyase, as well as Purification and Structural Analyses Thereof (2)

(1) Preparation

The sulfated fucoglucuronomannan oligosaccharides of the present invention were prepared by allowing the crude enzyme solution as described in Example 1 to act on the sulfated fucoglucuronomannan fraction derived from *Fucus vesiculosus* as described in Referential Example 4. Briefly, 0.61 g of the sulfated fucoglucuronomannan fraction derived from *Fucus vesiculosus* was dissolved in 60 ml of 20 mM phosphate buffer (pH 7.0) containing 400 mM sodium chloride. 6 ml of the crude enzyme solution as described in Example 1, which had been dialyzed against 20 mM imidazole-hydrochloride buffer (pH 7.0) containing 300 mM sodium chloride, 5 mM EDTA and 5 mM sodium azide, was then added thereto. The mixture was reacted at 25° C. for 7 days. A supernatant obtained by centrifuging the reaction mixture was subjected to ultrafiltration (exclusion molecular weight of 10,000) to collect a fraction of oligosaccharides having molecular weight of 10,000 or less. This fraction was designated as a sulfated fucoglucuronomannan enzymatic digestion product fraction 2.

(2) Purification

The sulfated fucoglucuronomannan enzymatic digestion product fraction 2 obtained in Example 3-(1) was concentrated to 40 ml. The concentrate was loaded onto a Cellulofine GCL-1000 (4×87 cm) equilibrated with 10% ethanol. Fractionation was carried out such that each fraction contained 10 ml of the eluate. The 70th to 100th fractions were collected, and desalted using a desalting apparatus (Micro Acilyzer G3, Asahi Kasei). Imidazole was added thereto at a final concentration of 10 mM. The resulting mixture was loaded onto a 80-ml DEAE-Cellulofine A-800 column equilibrated with 10 mM imidazole-hydrochloride buffer (pH 6.0). After washing with 160 ml of the same buffer, elution and collection were then carried out with a gradient of 0–800 mM sodium chloride. The absorbance at 232 nm was measured for each fraction. The total sugar content and the total uronic acid content of each fraction were measured according to the phenol-sulfuric acid method and the carbazole-sulfuric acid method, respectively. As a result, distinct five peaks for which the absorbance at 232 nm, the total sugar content and the total uronic acid content were proportional to each other were detected. The fractions in each peak were pooled and the pools were designated as oligosaccharide fractions 2-(1) to (5) according to the salt concentrations used for the elution (from low to high).

Each of the oligosaccharide fractions 2-(1) to (5) was concentrated to 4 ml using an evaporator, loaded onto a Cellulofine GCL-25 column (2×32 cm) equilibrated with 10% ethanol and eluted with 10% ethanol for desalting, and then dried. Thus, 3.5, 3.9, 1.9, 1.7 and 0.9 mg of the sulfated fucoglucuronomannan oligosaccharides 2-(1) to (5) of the present invention were obtained, respectively.

(3) Structural Analyses

The sulfated fucoglucuronomannan oligosaccharides 2-(1) to (5) of the present invention obtained in Example 3-(2) were subjected to analyses of saccharides at the reducing ends and saccharide compositions after fluorescence labeling with 2-aminopyridine. As a result, the saccharide at the reducing end for each of the sulfated fucoglucuronomannan oligosaccharides 2-(1) to (5) of the present invention was determined to be mannose. Regarding the neutral sugar composition, each oligosaccharide consisted of fucose and mannose. Next, determination of the sulfuric acid content (measured according to the turbidimetric method using barium chloride) and the uronic acid content (measured according to the carbazole-sulfuric acid method), mass spectrometric analysis using a mass spectrometer API-III (Perkin-Elmer Sciex) and NMR analysis using a nuclear magnetic resonance apparatus JNM-α500 (Nippon Denshi) were carried out. Samples to be analyzed were subjected to structural analyses after exchange for heavy water according to a conventional method. Bonds of constituting saccharides were analyzed using the HMBC method, a method for $^1$H-detection of heteronuclei. The DQF-COSY method and the HOHAHA method were used for assignment in $^1$H-NMR.

Physical properties of the sulfated fucoglucuronomannan oligosaccharides 2-(1) to (5) of the present invention are shown below.

(a) Physical properties of the sulfated fucoglucuronomannan oligosaccharide 2-(1) of the present invention As a result of the above-mentioned analyses, it was demonstrated that this substance was identical to the sulfated fucoglucuronomannan oligosaccharide 1-(1) of the present invention.

Figure 7:
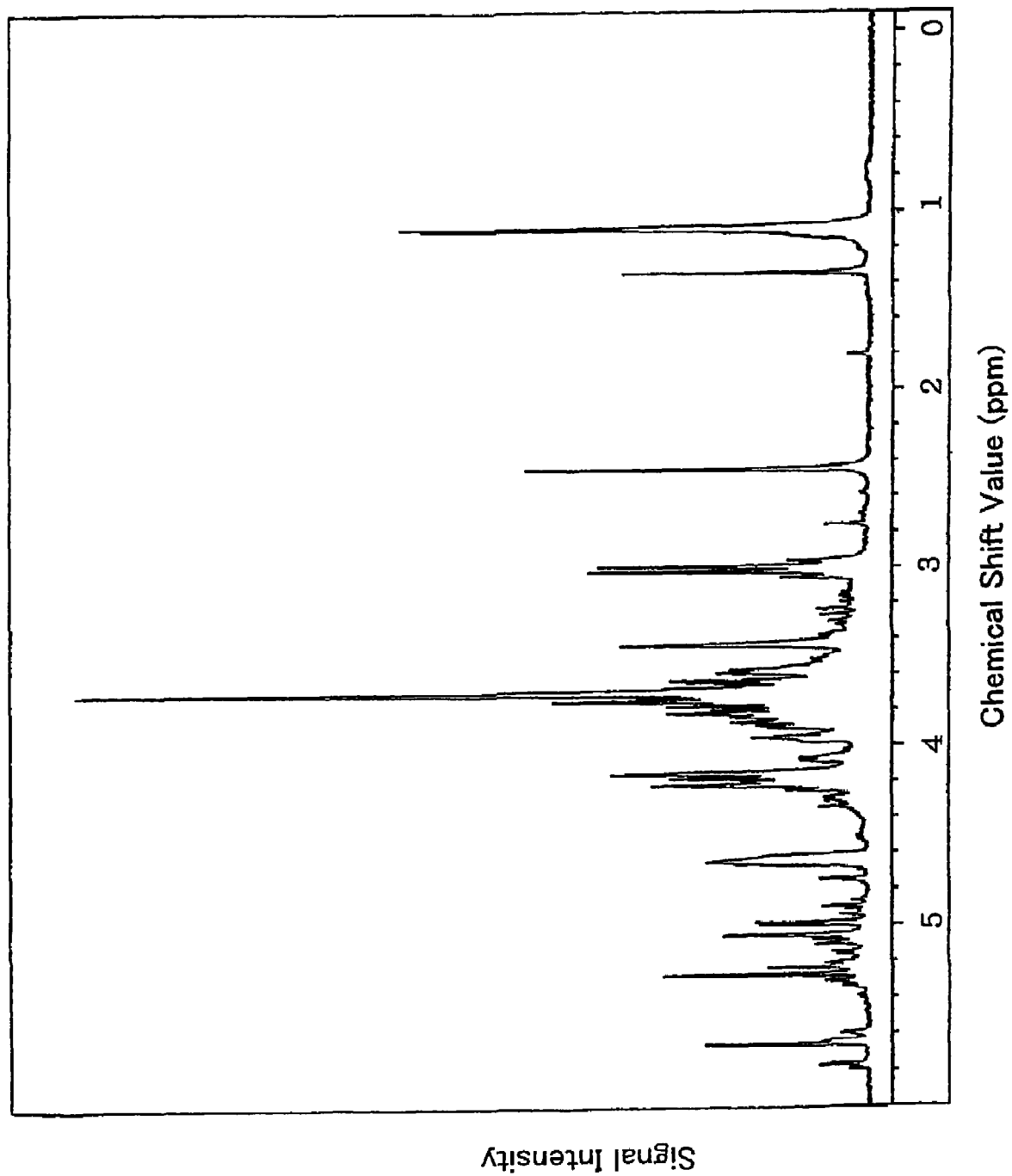
FIG. 7. a figure which illustrates the $^1$H-NMR spectrum of the sulfated fucoglucuronomannan oligosaccharide 2-(2) according to the present invention.
Figure 8:
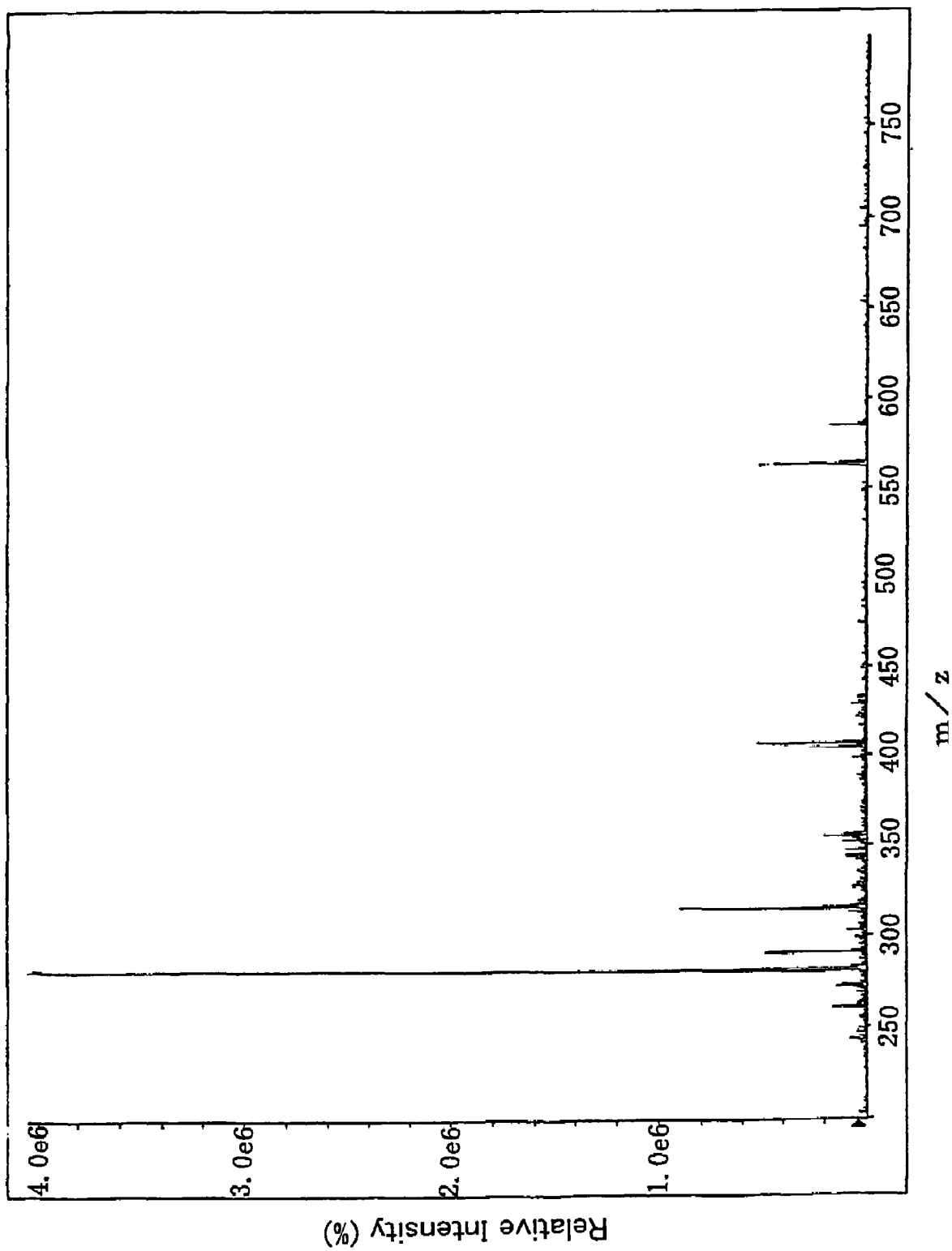
FIG. 8. a figure which illustrates the mass spectrum of the sulfated fucoglucuronomannan oligosaccharide 2-(2) according to the present invention.

(b) Physical properties of the sulfated fucoglucuronomannan oligosaccharide 2-(2) of the present invention The results for mass spectrometric analysis and assignment in NMR analyses are shown below. The $^1$H-NMR spectrum and mass spectrum are illustrated in FIGS. 7 and 8, respectively. In FIG. 7, the vertical axis represents the signal intensity and the horizontal axis represents the chemical shift value (ppm). In FIG. 8, the vertical axis represents the relative intensity and the horizontal axis represents the m/z value.

Molecular weight: 564

MS m/z 563.0 $[M-H^+]^-$, 585.0 $[M+Na^+-2H^+]^-$ 281.0 $[M-2H]^{2-}$

The results of $^1$H-NMR analyses are shown in Table 3.

TABLE 3

| | Chemical shift value (ppm) $^1$H-NMR Chemical shift value, multiplicity, coupling constant |
|---|---|
| F1-1 | 5.05, d, 4.0 |
| F1-2 | 3.75, m |
| F1-3 | 3.82, dd, 3.0, 11.0 |
| F1-4 | 3.71, m |
| F1-5 | 4.15, m |
| F1-6 | 1.10, d, 6.0 |
| M-1 | 5.27, s |
| M-2 | 4.22, m |
| M-3 | 3.88, dd, 2.5, 10.0 |
| M-4 | 3.78, t, 10.0 |
| M-5 | 3.95, m |
| M-6 | 4.15, m |
| | 4.22, m |
| ΔGA-1 | 4.99, d, 6.5 |
| ΔGA-2 | 3.63, t, 6.5 |
| ΔGA-3 | 4.15, m |
| ΔGA-4 | 5.66, d, 3.5 |
| ΔGA-5 | — |
| ΔGA-6 | — |

Saccharide composition: L-fucose:D-mannose:unsaturated glucuronic acid=1:1:1

Sulfate group: 1 molecule

The numbers for peak assignment in ¹H-NMR are as indicated in formula (V) below:

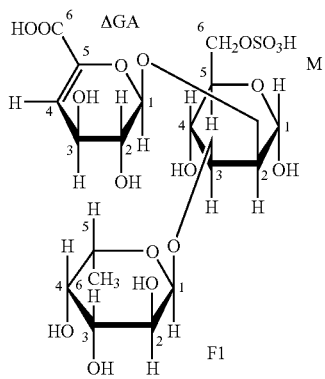

(V)

Figure 9:
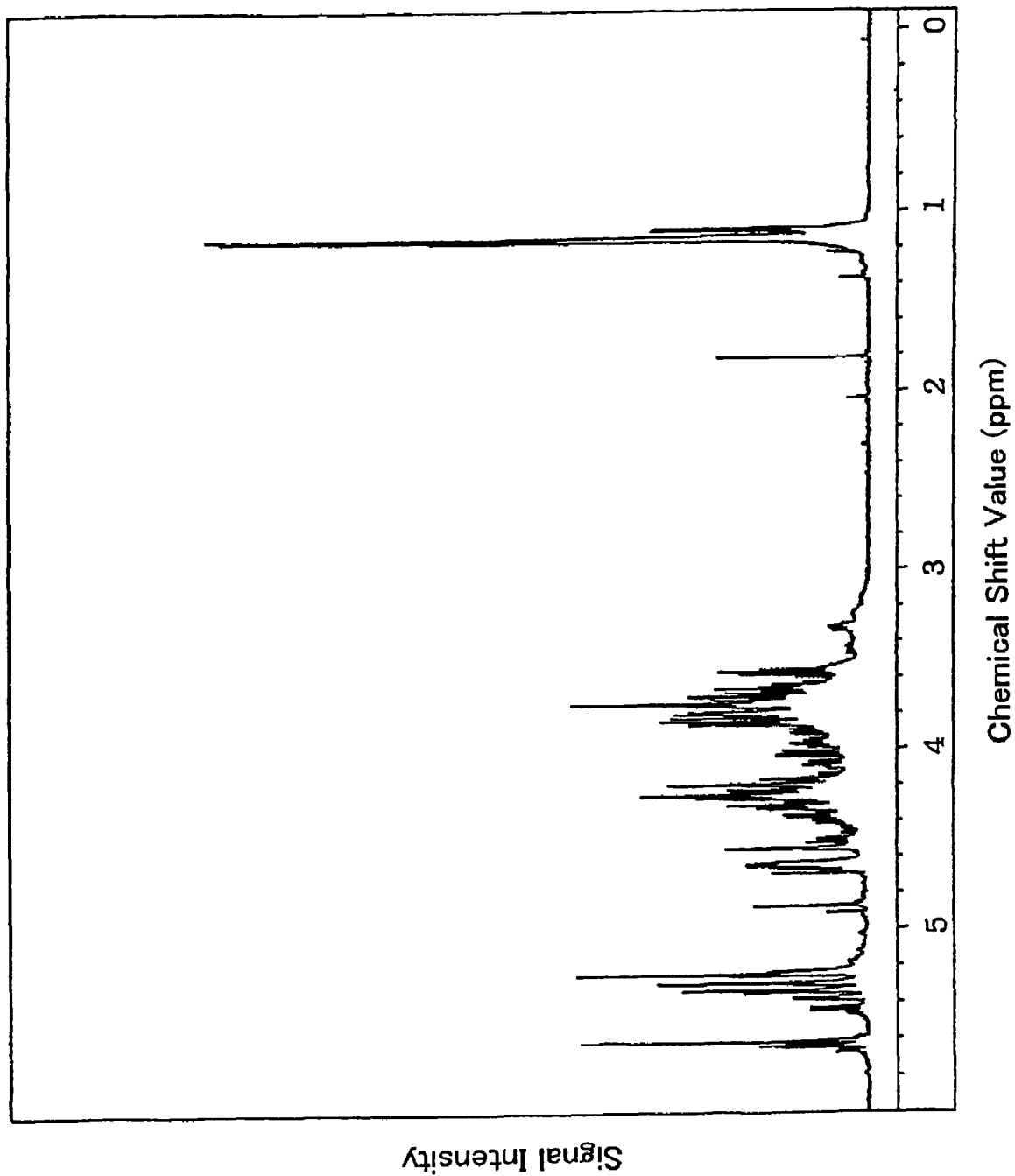
FIG. 9. a figure which illustrates the $^1$H-NMR spectrum of the sulfated fucoglucuronomannan oligosaccharide 2-(3) according to the present invention.
Figure 10:
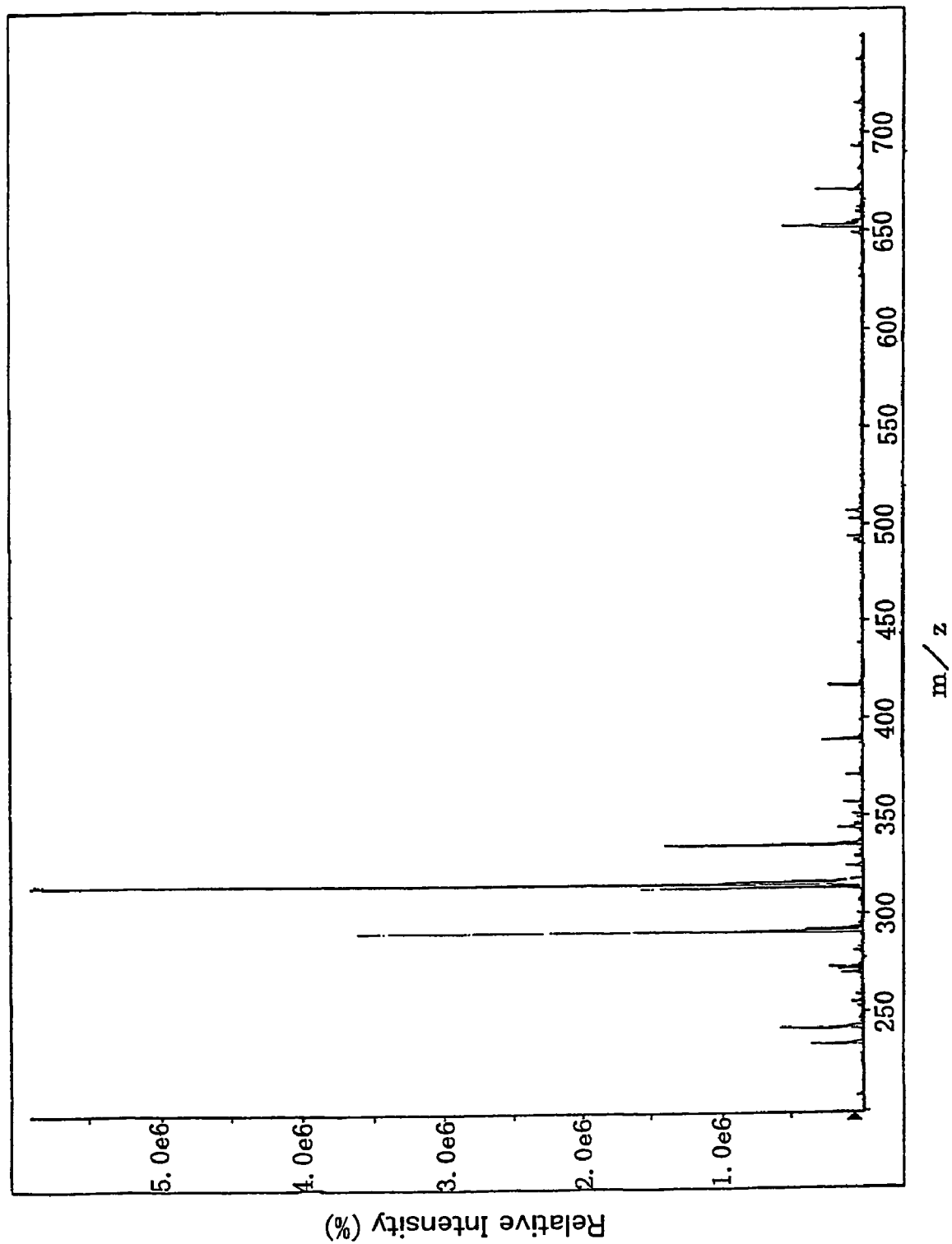
FIG. 10. a figure which illustrates the mass spectrum of the sulfated fucoglucuronomannan oligosaccharide 2-(3) according to the present invention.

(c) Physical properties of the sulfated fucoglucuronomannan oligosaccharide 2-(3) of the present invention The results for mass spectrometric analysis and assignment in NMR analyses are shown below. The ¹H-NMR spectrum and mass spectrum are illustrated in FIGS. 9 and 10, respectively. In FIG. 9, the vertical axis represents the signal intensity and the horizontal axis represents the chemical shift value (ppm). In FIG. 10, the vertical axis represents the relative intensity and the horizontal axis represents the m/z value.

Molecular weight: 644

MS m/z 321.3 $[M-2H+]^{2-}$

The results of ¹H-NMR analyses are shown in Table 4.

TABLE 4

| | Chemical shift value (ppm) ¹H-NMR Chemical shift value, multiplicity, coupling constant |
|---|---|
| F1-1 | 5.25, d, 3.5 |
| F1-2 | 4.32, dd, 3.5, 10.5 |
| F1-3 | 4.02, dd, 3.5, 10.5 |
| F1-4 | 4.55, d, 3.5 |
| F1-5 | 4.39, q, 6.5 |
| F1-6 | 1.16, d, 6.5 |
| M-1 | 5.29, d, 2.0 |
| M-2 | 4.20, dd, 2.0, 2.5 |
| M-3 | 3.86, dd, 2.5, 7.0 |
| M-4 | 3.75, m |
| M-5 | 3.75, m |
| M-6 | 3.75, m |
| ΔGA-1 | 5.45, d, 7.0 |
| ΔGA-2 | 3.57, t, 7.0 |
| ΔGA-3 | 4.27, dd, 3.5, 7.0 |
| ΔGA-4 | 5.62, d, 3.5 |
| ΔGA-5 | — |
| ΔGA-6 | — |

Saccharide composition: L-fucose:D-mannose:unsaturated glucuronic acid=1:1:1

Sulfate group: 2 molecules

The numbers for peak assignment in ¹H-NMR are as indicated in formula (VI) below:

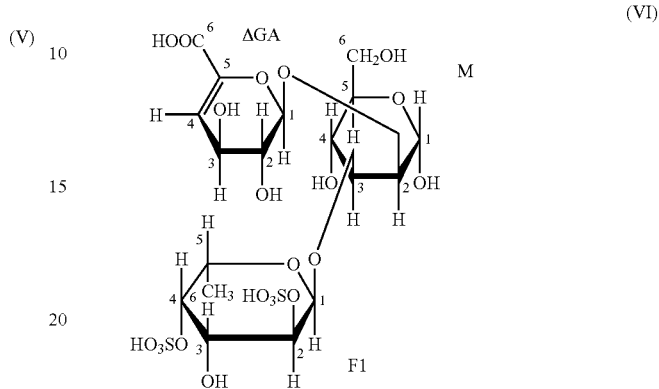

(VI)

Figure 11:
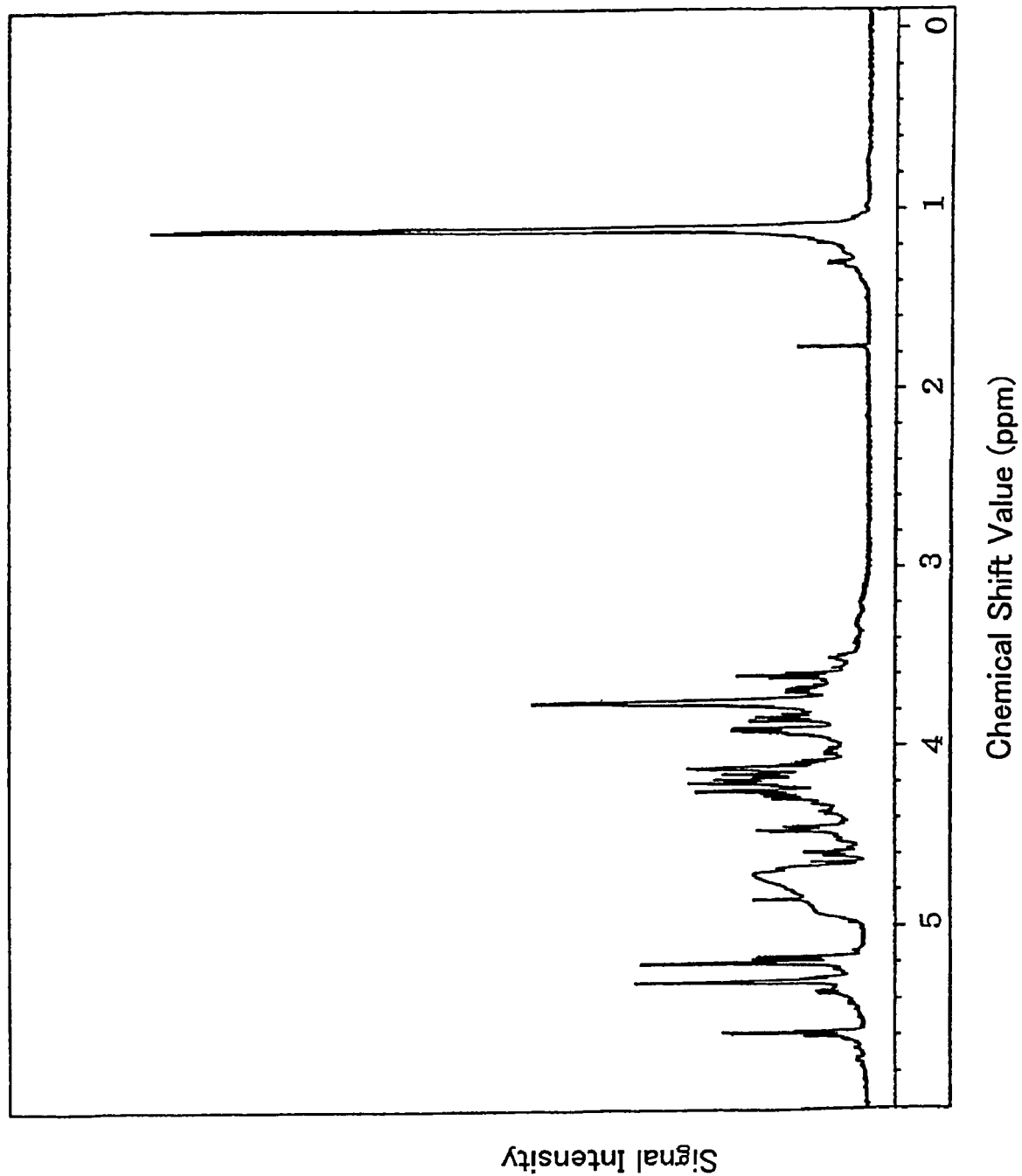
FIG. 11. a figure which illustrates the $^1$H-NMR spectrum of the sulfated fucoglucuronomannan oligosaccharide 2-(4) according to the present invention.
Figure 12:
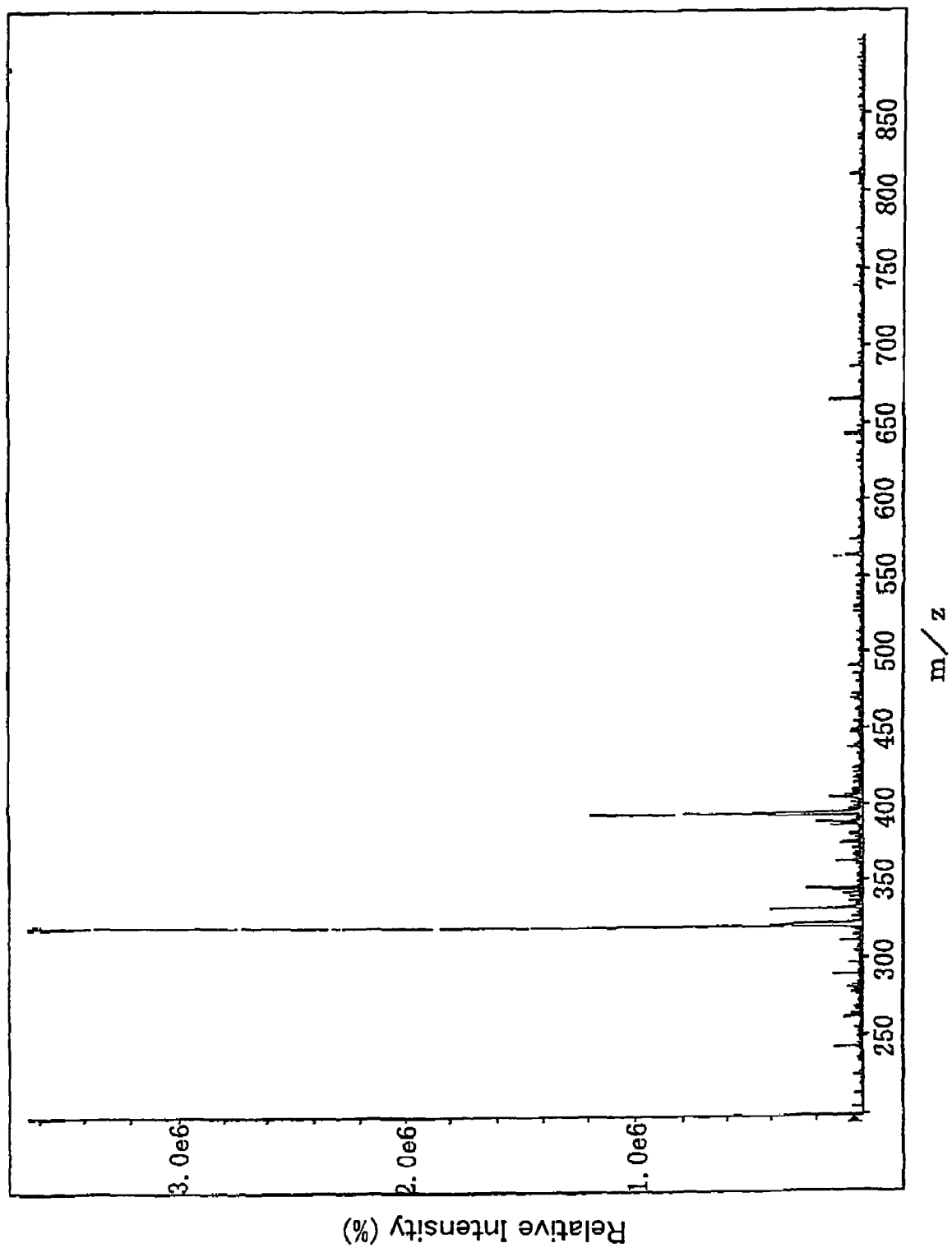
FIG. 12. a figure which illustrates the mass spectrum of the sulfated fucoglucuronomannan oligosaccharide 2-(4) according to the present invention.

(d) Physical properties of the sulfated fucoglucuronomannan oligosaccharide 2-(4) of the present invention The results for mass spectrometric analysis and assignment in NMR analyses are shown below. The ¹H-NMR spectrum and mass spectrum are illustrated in FIGS. 11 and 12, respectively. In FIG. 11, the vertical axis represents the signal intensity and the horizontal axis represents the chemical shift value (ppm). In FIG. 12, the vertical axis represents the relative intensity and the horizontal axis represents the m/z value.

Molecular weight: 870

MS m/z 456.1 $[M+2Na-4H^+]^{2-}$, 445.0 $[M+Na^+-3H^+]^{2-}$

The results of ¹H-NMR analyses are shown in Tables 5 and 6.

TABLE 5

| | Chemical shift value (ppm) ¹H-NMR Chemical shift value, multiplicity, coupling constant |
|---|---|
| F1-1 | 5.29, d, 4.0 |
| F1-2 | 4.45, dd, 4.0, 10.5 |
| F1-3 | 4.59, dd, 3.0, 10.5 |
| F1-4 | 4.15, d, 3.0 |
| F1-5 | 4.26, q, 6.0 |
| F1-6 | 1.10, d, 6.0 |
| F2-1 | 5.19, s |
| F2-2 | 4.12, m |
| F2-3 | 3.75, m |
| F2-4 | 3.75, m |
| F2-5 | 3.75, m |
| F2-6 | 1.10, d, 6.0 |

TABLE 6

| | Chemical shift value (ppm) ¹H-NMR Chemical shift value, multiplicity, coupling constant |
|---|---|
| M-1 | 5.30, d, 2.0 |
| M-2 | 4.24, m |
| M-3 | 3.91, m |
| M-4 | 3.83, t, 9.5 |

TABLE 6-continued

| | Chemical shift value (ppm) $^1$H-NMR Chemical shift value, multiplicity, coupling constant |
|---|---|
| M-5 | 3.91, m |
| M-6 | 4.09, dd, 6.0, 11.0 |
| | 4.18, m |
| ΔGA-1 | 5.17, d, 7.0 |
| ΔGA-2 | 3.60, t, 7.0 |
| ΔGA-3 | 4.19, dd, 3.0, 7.0 |
| ΔGA-4 | 5.58, d, 3.0 |
| ΔGA-5 | — |
| ΔGA-6 | — |

Saccharide composition: L-fucose:D-mannose:unsaturated glucuronic acid=2:1:1
Sulfate group: 3 molecules
The numbers for peak assignment in $^1$H-NMR are as indicated in formula (VII) below:

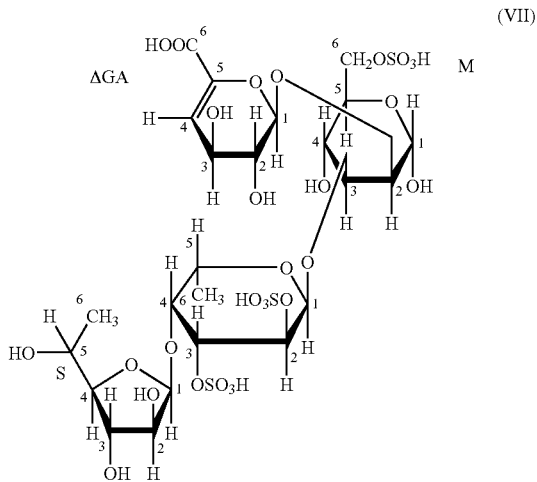
(VII)

Figure 13:
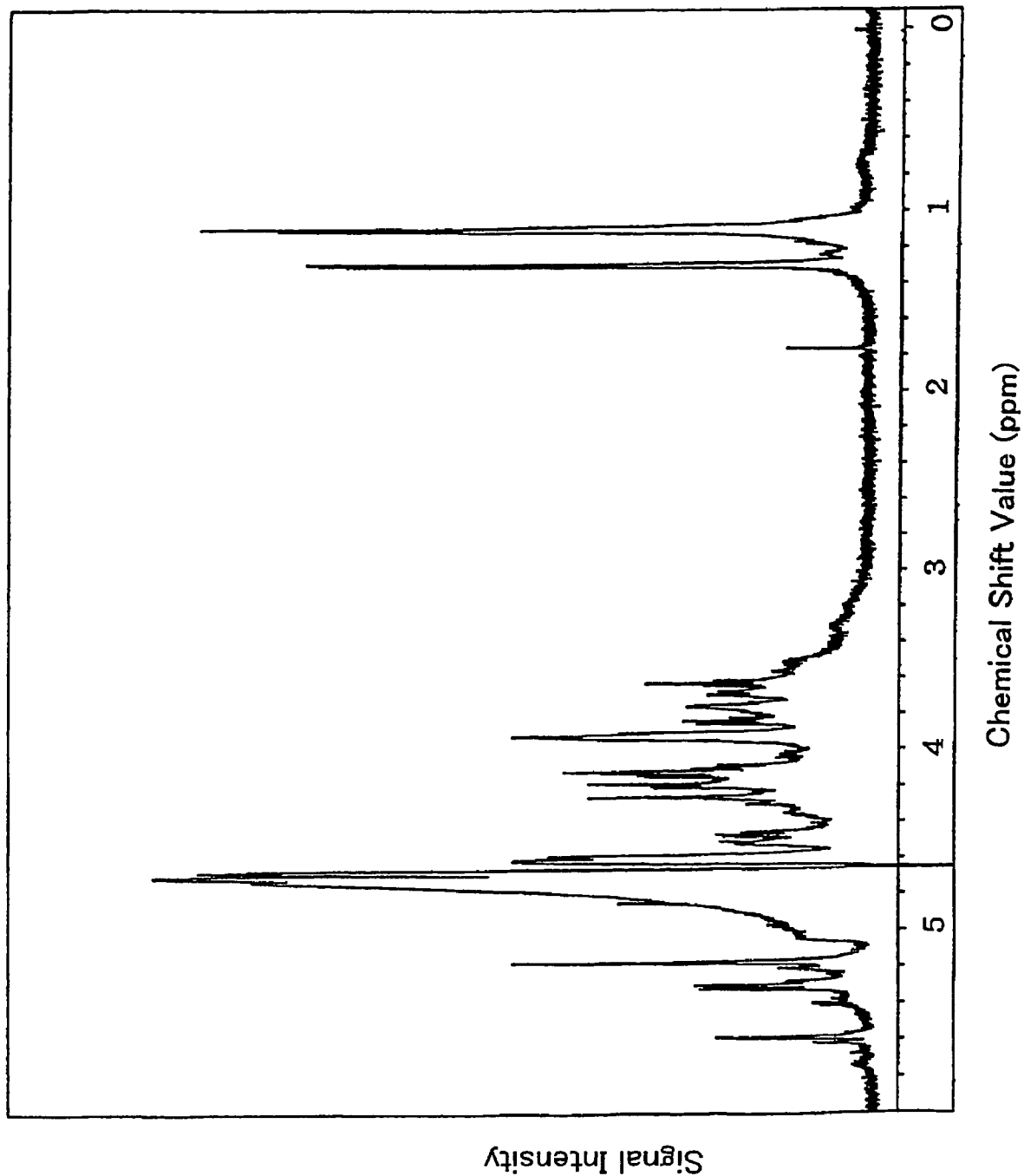
FIG. 13. a figure which illustrates the $^1$H-NMR spectrum of the sulfated fucoglucuronomannan oligosaccharide 2-(5) according to the present invention.
Figure 14:
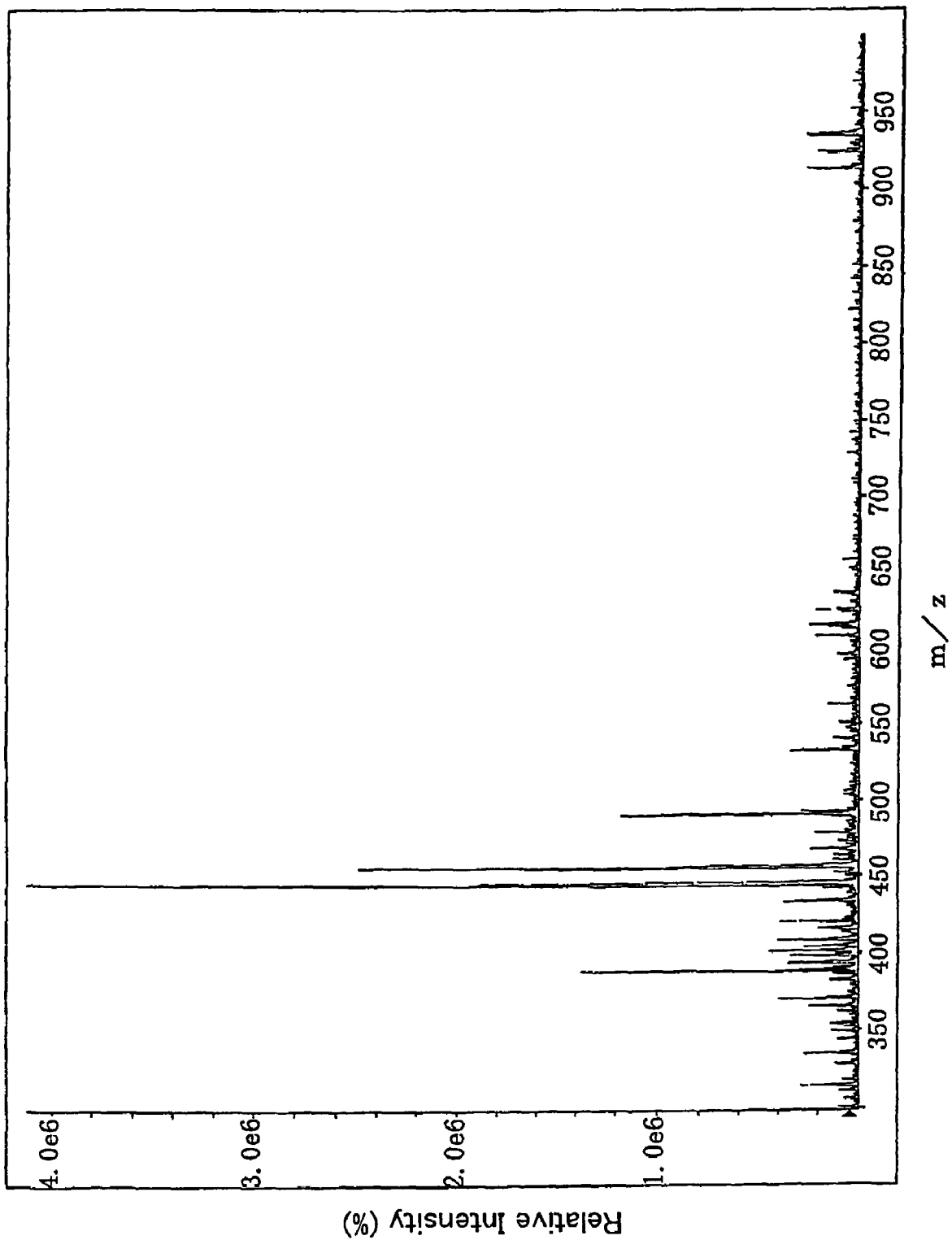
FIG. 14. a figure which illustrates the mass spectrum of the sulfated fucoglucuronomannan oligosaccharide 2-(5) according to the present invention.

(e) Physical properties of the sulfated fucoglucuronomannan oligosaccharide 2-(5) of the present invention The results for mass spectrometric analysis and assignment in NMR analyses are shown below. The $^1$H-NMR spectrum and mass spectrum are illustrated in FIGS. 13 and 14, respectively. In FIG. 13, the vertical axis represents the signal intensity and the horizontal axis represents the chemical shift value (ppm). In FIG. 14, the vertical axis represents the relative intensity and the horizontal axis represents the m/z value.

Molecular weight: 950

MS m/z 1037.0 [M+4Na−5H$^+$]$^-$, 506.9 [M+3Na−5H$^+$]$^{2-}$, 495.8 [M+2Na$^+$−4H$^+$]$^{2-}$

The results of $^1$H-NMR analyses are shown in Tables 7 and 8.

TABLE 7

| | Chemical shift value (ppm) $^1$H-NMR Chemical shift value, multiplicity, coupling constant |
|---|---|
| F1-1 | 5.30, d, 4.0 |
| F1-2 | 4.47, dd, 4.0, 11.0 |

TABLE 7-continued

| | Chemical shift value (ppm) $^1$H-NMR Chemical shift value, multiplicity, coupling constant |
|---|---|
| F1-3 | 4.61, m |
| F1-4 | 4.15, d, 2.5 |
| F1-5 | 4.28, m |
| F1-6 | 1.11, d, 6.0 |
| F2-1 | 5.18, s |
| F2-2 | 4.12, m |
| F2-3 | 3.93, m |
| F2-4 | 3.93, m |
| F2-5 | 4.52, dq, 1.5, 6.5 |
| F2-6 | 1.30, d, 6.5 |

TABLE 8

| | Chemical shift value (ppm) $^1$H-NMR Chemical shift value, multiplicity, coupling constant |
|---|---|
| M-1 | 5.32, d, 2.0 |
| M-2 | 4.26, m |
| M-3 | 3.93, m |
| M-4 | 3.84, t, 9.5 |
| M-5 | 3.93, m |
| M-6 | 4.10, dd, 7.0, 11.5 |
| | 4.20, m |
| ΔGA-1 | 5.17, d, 7.0 |
| ΔGA-2 | 3.63, t, 7.0 |
| ΔGA-3 | 4.19, m |
| ΔGA-4 | 5.59, d, 3.0 |
| ΔGA-5 | — |
| ΔGA-6 | — |

Saccharide composition: L-fucose:D-mannose:unsaturated glucuronic acid=2:1:1

Sulfate group: 4 molecules

The numbers for peak assignment in $^1$H-NMR are as indicated in formula (VIII) below:

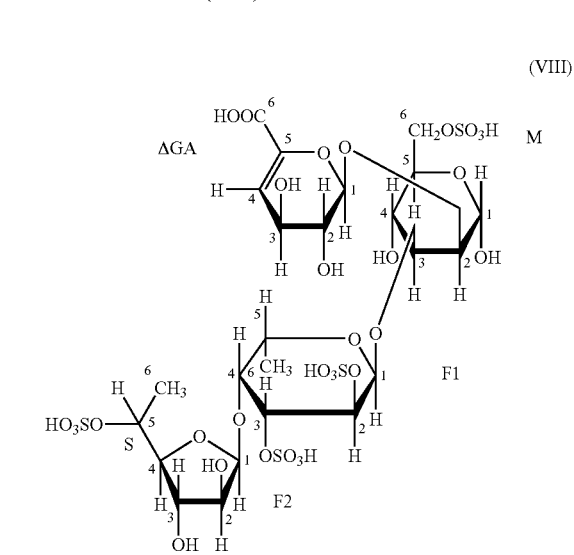
(VIII)

Example 4

Preparation of Sulfated Fucoglucuronomannan Oligosaccharides Using Recombinant Sulfated Fucoglucuronomannan Lyase, as well as Purification and Structural Analyses Thereof (1) Preparation The sulfated fucoglucuronomannan oligosaccharides of the present invention were prepared by allowing the recombinant sulfated fucoglucuronomannan lyase, which was produced by transferring a gene for the sulfated fucoglucuronomannan lyase as described in WO 99/11797 into *Escherichia coli*, to act on the sulfated fucoglucuronomannan fraction as described in Referential Example 4. Briefly, 0.4 g of the sulfated fucoglucuronomannan fraction derived from *Fucus vesiculosus* was dissolved in 40 ml of 20 mM imidazole-hydrochloride buffer (pH 7.0) containing 400 mM sodium chloride. 5 ml of a solution of the recombinant sulfated fucoglucuronomannan lyase (corresponding to 66 U) was then added thereto. The mixture was reacted at 25° C. for 25 hours. The reaction mixture was loaded onto a Cellulofine GCL-1000 column (4×87 cm) equilibrated with 10% ethanol. Fractionation was carried out such that each fraction contained 9.5 ml of the eluate. The 83rd to 120th fractions were pooled, and the pool was designated as a sulfated fucoglucuronomannan enzymatic digestion product fraction 3.

(2) Purification

The sulfated fucoglucuronomannan enzymatic digestion product fraction 3 obtained in Example 4-(1) was desalted using a desalting apparatus (Micro Acilyzer G3, Asahi Kasei). Imidazole was added thereto at final a concentration of 10 mM. The resulting mixture was loaded onto a 20-ml DEAE-Cellulofine A-800 column equilibrated with 10 mM imidazole-hydrochloride buffer (pH 6.0). After washing with 40 ml of the same buffer, elution was then carried out with a gradient of 0–800 mM sodium chloride. The absorbance at 232 nm was measured for each fraction. The total sugar content and the total uronic acid content of each fraction were measured according to the phenol-sulfuric acid method and the carbazole-sulfuric acid method, respectively. As a result, peaks for which the absorbance at 232 nm, the total sugar content and the total uronic acid content were proportional to each other were detected at portions eluted with 200 mM and 300 mM sodium chloride. The fractions in each peak were pooled and the pools were designated as oligosaccharide fractions 3-(1) and 3-(2).

The oligosaccharide fraction 3-(1) was concentrated to 1 ml using an evaporator, loaded onto a Cellulofine GCL-25 column (1.2×30 cm) equilibrated with 10% ethanol and eluted with 10% ethanol for desalting, and then dried. Thus, 0.7 mg of the sulfated fucoglucuronomannan oligosaccharide 3-(1) of the present invention was obtained.

The oligosaccharide fraction 3-(2) was concentrated to 1.0 ml using an evaporator, loaded onto a Cellulofine GCL-25 column (1.2×30 cm) equilibrated with 10% ethanol, eluted with 10% ethanol for desalting, and then dried. Thus, 1.6 mg of the sulfated fucoglucuronomannan oligosaccharide 3-(2) of the present invention was obtained.

(3) Structural Analyses

The sulfated fucoglucuronomannan oligosaccharides 3-(1) and 3-(2) of the present invention obtained in Example 4-(2) were subjected to analyses of saccharides at the reducing ends and saccharide compositions after fluorescence labeling with 2-aminopyridine. As a result, the saccharide at the reducing end for each of the sulfated fucoglucuronomannan oligosaccharides 3-(1) and 3-(2) of the present invention was determined to be mannose. Regarding the neutral sugar composition, each oligosaccharide consisted of fucose and mannose. Next, determination of the sulfuric acid content (measured according to the turbidimetric method using barium chloride) and the uronic acid content (measured according to the carbazole-sulfuric acid method), mass spectrometric analysis using a mass spectrometer API-III (Perkin-Elmer Sciex) and NMR analysis using a nuclear magnetic resonance apparatus JNM-α500 (Nippon Denshi) were carried out. Samples to be analyzed were subjected to structural analyses after exchange for heavy water according to a conventional method. Bonds of constituting saccharides were analyzed using the HMBC method, a method for $^1$H-detection of heteronuclei. The DQF-COSY method and the HOHAHA method were used for assignment in $^1$H-NMR.

Physical properties of the sulfated fucoglucuronomannan oligosaccharides 3-(1) and 3-(2) of the present invention are shown below.

(a) Physical Properties of the Sulfated Fucoglucuronomannan Oligosaccharide 3-(1) of the Present Invention As a result of the above-mentioned analyses, it was demonstrated that this substance had the same structure as that of an oligosaccharide previously reported.

The structure is shown as formula (IX) below:

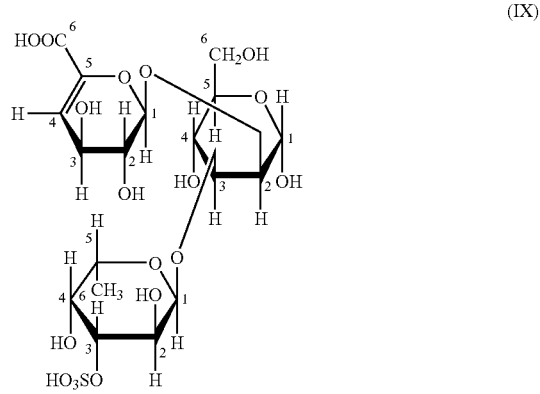

(IX)

(b) Physical Properties of the Sulfated Fucoglucuronomannan Oligosaccharide 3-(2) of the Present Invention As a result of the above-mentioned analyses, it was demonstrated that this substance was identical to the sulfated fucoglucuronomannan oligosaccharide 2-(3) of the present invention.

The results of Example 3 were compared with those of Example 4. Although a 200-fold or more amount of the sulfated fucoglucuronomannan lyase was used in Example 4, the efficiency of oligosaccharide generation on the basis of the substrate weight was less than one fifth. Furthermore, six kinds of oligosaccharides were obtained in Example 3, while only two kinds of oligosaccharides were obtained in Example 4. Thus, the sulfated fucoglucuronomannan lyase of the present invention efficiently degrades a sulfated fucoglucuronomannan derived from Fucus vesiculosus whereas the recombinant sulfated fucoglucuronomannan lyase used in Example 4 cannot degrade the sulfated fucoglucuronomannan derived from Fucus vesiculosus so efficiently.

Example 5

Determination of Molecular Weight of the Sulfated Fucoglucuronomannan Lyase of the Present Invention The crude enzyme solution of the sulfated fucoglucuronomannan lyase as described in Example 1 was subjected to gel filtration using a Sephacryl S-200 column (4.4×100 cm) equilibrated with 10 mM imidazole-hydrochloride buffer (pH 7.5) containing 100 mM sodium chloride, 10 mM calcium chloride and 5 mM sodium azide, and fractionated such that each fraction contained 13.5 ml of the eluate. The activity of the sulfated fucoglucuronomannan lyase of the present invention was measured for each fraction according to the method as described in Referential Example 7. Thus, the molecular weight of the sulfated fucoglucuronomannan lyase of the present invention was determined to be about 500,000 to 600,000.

Example 6

Preparation of Fucoidan Fraction Containing Less Molecular Species

In order to prepare a fucoidan fraction containing less molecular species using the sulfated polysaccharide mixture fraction derived from Fucus vesiculosus as described in Referential Example 1, 500 ml of 50 mM phosphate buffer (pH 7.0), 50 ml of 4 M sodium chloride, 10 ml of the crude enzyme solution of the sulfated fucoglucuronomannan lyase as described in Example 1 and 5 g of the sulfated polysaccharide fraction derived from Fucus vesiculosus as described in Referential Example 1 were mixed together, and the mixture was reacted at 25° C. for 5 days. Sulfated fucoglucuronomannan oligosaccharides resulted from the degradation were removed by dialysis to prepare the fucoidan fraction containing less molecular species of the present invention in which a sulfated fucoglucuronomannan was removed from the sulfated polysaccharide fraction.

Example 7

Structure of Site of Action for Sulfated Fucoglucuronomannan Lyase

The saccharide at the reducing end of each oligosaccharide generated using the sulfated fucoglucuronomannan lyase of the present invention was mannose. Unsaturated glucuronic acid was present at the nonreducing end. The absorbance at 232 nm was increased as the reaction proceeds. Therefore, it was assumed that this is an enzyme that cleaves a mannosyl bond between mannose and glucuronic acid in a sulfated fucoglucuronomannan eliminatively like the one as described in WO 96/34004.

If it is the enzyme as assumed, there should be a polysaccharide having a structure in which fucose side chains are extended from mannose in a sugar chain composed of glucuronic acid and mannose alternately bound to each other (a sulfated fucoglucuronomannan) in the fucoidan derived from Fucus vesiculosus. Oxalic acid treatment is a known method for obtaining a polysaccharide consisting of mannose and glucuronic acid (glucuronomannan) from a sulfated polysaccharide mixture derived from a brown alga (Carbohydrate Research, vol. 125, 283–290 (1984)). A fucoidan derived from Fucus vesiculosus was treated with reference to this method to analyze its structure in order to confirm if a sulfated fucoglucuronomannan was contained in Fucus vesiculosus as assumed.

Specifically, 1 g of the sulfated polysaccharide mixture fraction derived from Fucus vesiculosus prepared as described in Referential Example 1 was dissolved in 100 ml of water. 4.5 g of oxalic acid was added thereto. The pH was adjusted to 1.0 with 6 M sodium hydroxide. The mixture was treated at 100° C. for 5 hours. The pH was adjusted to 8 with 6 M sodium hydroxide. Ethanol was added at final concentration of 85% to a supernatant obtained by centrifugation. After allowing to stand for 2 hours, the mixture was centrifuged to obtain a precipitate. The precipitate was dissolved in 3000 ml of 10 mM imidazole-hydrochloride buffer (pH 8.0). The solution was loaded onto 100-ml DEAE-Cellulofine equilibrated with 10 mM imidazole-hydrochloride buffer (pH 8.0) containing 30 mM sodium chloride. After washing with the same buffer, elution was carried out with a gradient of 30 mM to 500 mM sodium chloride. Fractionation was carried out such that each fraction contained 10 ml of the eluate. The neutral sugar content and the uronic acid content of each fraction were measured according to the phenol-sulfuric acid method and the carbazole-sulfuric acid method, respectively. The main component containing neutral sugar and uronic acid was eluted with 120–250 mM sodium chloride. The fraction was collected, desalted using a electrodialysis device, lyophilized, and subjected to NMR analysis after exchange for heavy water. As a result, it was confirmed that this substance had the same structure as that of glucuronomannan as described in Carbohydrate Research, vol. 125, 283–290 (1984).

Thus, it was shown that the unsaturated glucuronic acid contained in the oligosaccharide of the present invention was generated from glucuronic acid in the sulfated fucoglucuronomannan by the action of the sulfated fucoglucuronomannan lyase of the present invention.

In addition, it was shown that the fucoidan derived from Fucus vesiculosus contained a novel sulfated fucoglucuronomannan which contained fucofuranose.

Industrial Applicability

The present invention provides a novel sulfated fucoglucuronomannan lyase which can be used for structural analysis of a sulfated fucoglucuronomannan and reproducible production of a sulfated fucoglucuronomannan oligosaccharide as well as a method for producing the enzyme. The present invention further provides a sulfated fucoglucuronomannan oligosaccharide and a fucoidan fraction containing less molecular species which can be produced using the enzyme and are useful as reagents for glycotechnology as well as methods for producing the same.

Sequence Listing Free Text
SEQ ID NO:1: 16S rDNA region of *Fucophilus fucoidanolyticus* SI-1234

What is claimed is:
1. A sulfated fucoglucuronomannan oligosaccharide of formula (II), or a salt thereof:
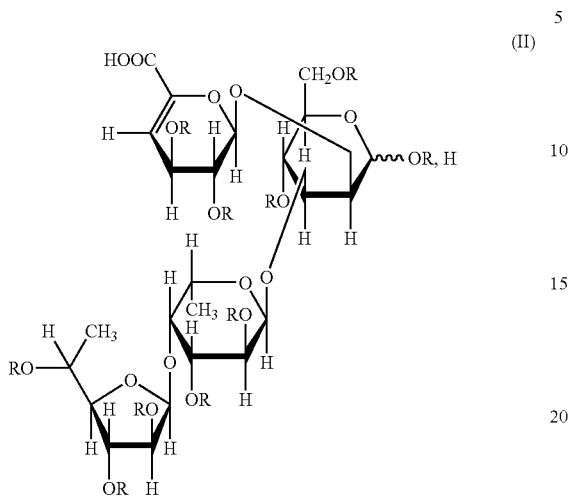
(II)
wherein R is H or SO$_3$H.
* * * * *